(12) United States Patent
Cassayre et al.

(10) Patent No.: US 9,439,431 B2
(45) Date of Patent: Sep. 13, 2016

(54) PESTICIDAL MIXTURES COMPRISING ISOXAZOLINE DERIVATIVES

(75) Inventors: Jerome Yves Cassayre, Stein (CH); Myriem El Qacemi, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/119,895

(22) PCT Filed: May 30, 2012

(86) PCT No.: PCT/EP2012/060103
§ 371 (c)(1),
(2), (4) Date: Nov. 25, 2013

(87) PCT Pub. No.: WO2012/163945
PCT Pub. Date: Dec. 6, 2012

(65) Prior Publication Data
US 2014/0135216 A1 May 15, 2014

(30) Foreign Application Priority Data

May 31, 2011 (EP) .................................. 11168220

(51) Int. Cl.
| A01N 43/80 | (2006.01) |
| A01N 43/54 | (2006.01) |
| A01N 43/56 | (2006.01) |
| A01N 43/653 | (2006.01) |

(52) U.S. Cl.
CPC .............. *A01N 43/80* (2013.01); *A01N 43/54* (2013.01); *A01N 43/56* (2013.01); *A01N 43/653* (2013.01)

(58) Field of Classification Search
CPC ...... A01N 43/54; A01N 43/80; A01N 43/56; A01N 43/653
See application file for complete search history.

(56) References Cited

U.S. PATENT DOCUMENTS 8,735,362 B2 * 5/2014 Cassayre et al. ............... 514/30

FOREIGN PATENT DOCUMENTS

| EP | 1731512 | | 12/2006 |
| WO | WO2007048556 | | 5/2007 |
| WO | WO 2010/020521 | * | 2/2010 |
| WO | WO2011067272 | | 6/2011 |
| WO | WO 2011/101402 | * | 8/2011 |

OTHER PUBLICATIONS

Azoxystrobin Pesticide Info, British Columbia Ministry of Agriculture and Lands, Jan. 2009.*
International Search Report and Written Opinion for International Patent Application No. PCT/EP2012/060103 dated Oct. 17, 2012.

* cited by examiner

*Primary Examiner* — John Pak
(74) *Attorney, Agent, or Firm* — R. Kody Jones

(57) ABSTRACT

The present invention relates to pesticidal mixtures comprising a component A and a component B, wherein component A is a compound of formula (I) wherein $A^1$, $A^2$, L, p, $R^1$, $R^2$, $R^3$, $R^4$ and $R^5$ are as defined in claim 1 and component B is a fungicide. The present invention also relates to methods of using said mixtures for the control of plant pests.

(I)

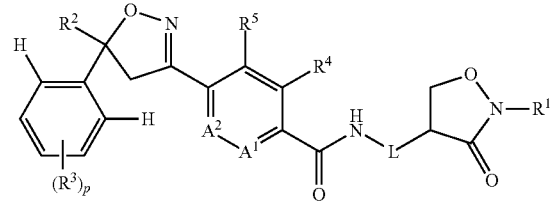

9 Claims, No Drawings

PESTICIDAL MIXTURES COMPRISING ISOXAZOLINE DERIVATIVES

RELATED APPLICATION INFORMATION

This application is a 371 of International Application No. PCT/EP2012/060103, filed 30 May 2012, which claims the benefit of European Patent Application No. 11168220.9, filed 31 May 2011, the contents of which are incorporated herein by reference.

The present invention relates to mixtures of pesticidally active ingredients and to methods of using the mixtures in the field of agriculture.

EP1731512 discloses that certain isoxazoline compounds have insecticidal activity.

The present invention provides pesticidal mixtures comprising a component A and a component B, wherein component A is a compound of formula I

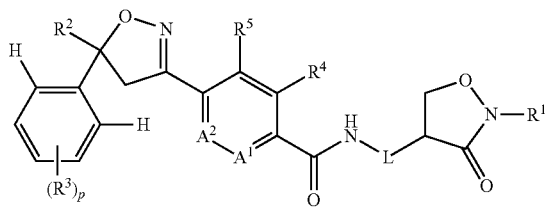

wherein
L is a direct bond or methylene;
$A^1$ and $A^2$ are C—H, or one of $A^1$ and $A^2$ is C—H and the other is N;
$R^1$ is hydrogen, cyano, cyano-$C_1$-$C_8$alkyl, $C_1$-$C_8$alkyl, $C_1$-$C_8$haloalkyl, $C_3$-$C_8$cycloalkyl, $C_3$-$C_8$cycloalkyl where one carbon atom is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_3$-$C_8$cycloalkyl-$C_1$-$C_8$haloalkyl, $C_1$-$C_8$hydroxyalkyl, $C_1$-$C_8$alkoxy-$C_1$-$C_8$alkyl, $C_2$-$C_8$alkenyl, $C_2$-$C_8$haloalkenyl, $C_2$-$C_8$alkynyl, $C_2$-$C_8$haloalkynyl, phenyl, phenyl substituted by one to three $R^6$, phenyl-$C_1$-$C_4$alkyl, phenyl-$C_1$-$C_4$alkyl wherein the phenyl moiety is substituted by one to three $R^6$, 5-6 membered heteroaryl-$C_1$-$C_4$alkyl or 5-6 membered heteroaryl-$C_1$-$C_4$alkyl wherein the heteroaryl moiety is substituted by one to three $R^6$, or $C_1$-$C_4$alkyl-($C_1$-$C_4$alkyl-O—N=)C—$CH_2$—;
$R^2$ is chlorodifluoromethyl or trifluoromethyl;
each $R^3$ is independently bromo, chloro, fluoro or trifluoromethyl;
$R^4$ is hydrogen, halogen, methyl, halomethyl or cyano;
$R^5$ is hydrogen;
or $R^4$ and $R^5$ together form a bridging 1,3-butadiene group;
each $R^6$ is independently fluoro, chloro, bromo, trifluoromethyl, trifluoromethoxy, cyano or methoxy.
p is 2 or 3;
and component B is a fungicide selected from
a strobilurin fungicide including those selected from the group consisting of:
Azoxystrobin, Dimoxystrobin, Enestrobin, Fluoxastrobin, Kresoxim-methyl, Metominostrobin, Orysastrobin, Picoxystrobin, Pyraclostrobin and Trifloxystrobin;
an azole fungicide including those selected from the group consisting of:
Azaconazole, Bromuconazole, Cyproconazole, Difenoconazole, Diniconazole, Diniconazole-M, Epoxiconazole, Fenbuconazole, Fluquinconazole, Flusilazole, Flutriafol, Hexaconazole, Imazalil, Imibenconazole, Ipconazole, Metconazole, Myclobutanil, Oxpoconazole, Pefurazoate, Penconazole, Prochloraz, Propiconazole, Prothioconazole, Simeconazole, Tebuconazole, Tetraconazole, Triadimefon, Triadimenol, Triflumizole, Triticonazole, Diclobutrazol, Etaconazole, Furconazole, Furconazole-cis, Thiabendazole and Quinconazole;
a phenyl pyrrole fungicide including those selected from the group consisting of: Fenpiclonil and Fludioxonil;
an anilino-pyrimidine fungicide including those selected from the group consisting of: Cyprodinil, Mepanipyrim and Pyrimethanil;
a morpholine fungicide including those selected from the group consisting of: Aldimorph, Dodemorph, Fenpropimorph, Tridemorph, Fenpropidin and Spiroxamine;
a carboxamide fungicide including those selected from the group consisting of: Isopyrazam, Sedaxane, Bixafen, Penthiopyrad, Fluxapyroxad, Boscalid, Penflufen, Fluopyram, a compound of formula IIA

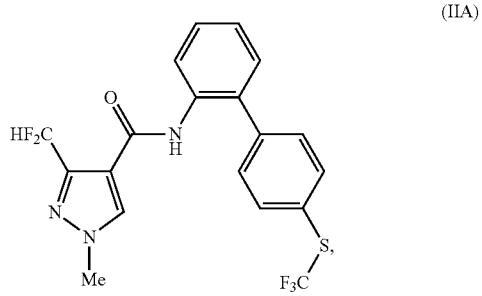

a compound of formula IIIA

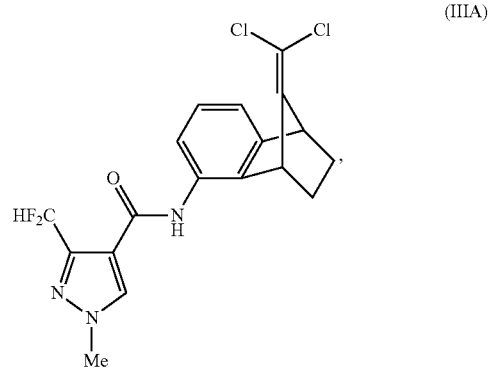

and a compound of formula IVA

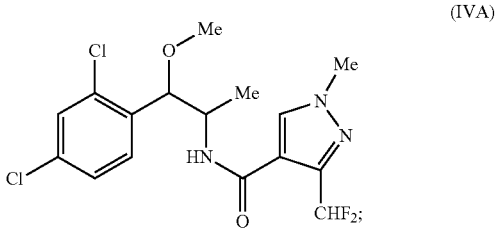 [SMILES: COC(c1ccc(Cl)cc1Cl)C(C)NC(=O)c1cn(C)nc1C(F)F]

a carboxylic acid amide fungicide including those selected from the group consisting of: Mandipropamid, Benthiavalicarb and Dimethomorph;

Chlorothalonil, Fluazinam, Dithianon, Metrafenone, Tricyclazole, Mefenoxam, Metalaxyl, Acibenzolar, Mancozeb, Ametoctradine and Cyflufenamid.

Compounds of formula I are known to have insecticidal activity, whereas compounds of component B are known to have fungicidal activity. Certain active ingredient mixtures of a compound of formula I and a fungicide can enhance the spectrum of action with respect to the pest to be controlled, e.g. the animal pest and/or the fungal pest. For example, the combination of A and B may cause an increase in the insecticidal action of component A and/or an increase in the fungicidal action of component B which would be expected from each component when used alone. This allows, on the one hand, a substantial broadening of the spectrum of pests that can be controlled and, on the other hand, increased safety in use through lower rates of application.

However, besides the actual synergistic action with respect to pest control, the pesticidal mixtures according to the invention can have further advantageous properties which can also be described, in a wider sense, as synergistic activity. Examples of such advantageous properties that may be mentioned are: a broadening of the spectrum of activity; a reduction in the rate of application of the active ingredients; adequate pest control with the aid of the mixtures according to the invention, sometimes even at a rate of application at which the individual compounds are totally ineffective; advantageous behaviour during formulation and/or upon application, for example upon grinding, sieving, emulsifying, dissolving or dispensing; increased storage stability; improved stability to light; more advantageous degradability; improved toxicological and/or ecotoxicological behaviour; improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination; or any other advantages familiar to a person skilled in the art.

The compounds of formula I have outstanding insecticidal properties as described in PCT/EP2010/068605. The components B are known and have the following CAS numbers: Azoxystrobin (131860-33-8), Dimoxystrobin (149961-52-4), Enestrobin (238410-11-2), Fluoxastrobin (193740-76-0), Kresoxim-methyl (143390-89-0), Metominostrobin (133408-50-1), Orysastrobin (248593-16-0), Picoxystrobin (117428-22-5), Pyraclostrobin (175013-18-0), trifloxystrobin (141517-21-7), Azaconazole (60207-31-0), Bromuconazole (116255-48-2), Cyproconazole (94361-06-5), Difenoconazole (119446-68-3), Diniconazole (83657-24-3), Diniconazole-M (83657-18-5), Epoxiconazole (13385-98-8), Fenbuconazole (114369-43-6), Fluquinconazole (136426-54-5), Flusilazole (85509-19-9), Flutriafol (76674-21-0), Hexaconazole (79983-71-4), Imazalil (58594-72-2), Imibenconazole (86598-92-7), Ipconazole (125225-28-7), Metconazole (125116-23-6), Myclobutanil (88671-89-0), Oxpoconazole (174212-12-5), Pefurazoate (58011-68-0), Penconazole (66246-88-6), Prochloraz (67747-09-5), Propiconazole (60207-90-1), Prothioconazole (178928-70-6), Simeconazole (149508-90-7), Tebuconazole (107534-96-3), Tetraconazole (112281-77-3), Triadimefon (43121-43-3), Triadimenol (55219-65-3), Triflumizole (99387-89-0), Triticonazole (131983-72-7), Diclobutrazol (76738-62-0), Etaconazole (60207-93-4), Fluconazole (86386-73-4), Fluconazole-cis (112839-32-4), Thiabendazole (148-79-8), Quinconazole (103970-75-8), Fenpiclonil (74738-17-3), Fludioxonil (131341-86-1), Cyprodinil (121552-61-2), Mepanipyrim (110235-47-7), Pyrimethanil (53112-28-0), Aldimorph (91315-15-0), Dodemorph (1593-77-7), Fenpropimorph (67564-91-4), Tridemorph (81412-43-3), Fenpropidin (67306-00-7), Spiroxamine (118134-30-8), Isopyrazam (881685-58-1), Sedaxane (874967-67-6), Bixafen (581809-46-3), Penthiopyrad (183675-82-3), Fluxapyroxad (907204-31-3), Boscalid (188425-85-6), Penflufen (494793-67-8), Fluopyram (658066-35-4), Mandipropamid (374726-62-2), Benthiavalicarb (413615-35-7), Dimethomorph (110488-70-5), Chlorothalonil (1897-45-6), Fluazinam (79622-59-6), Dithianon (3347-22-6), Metrafenone (220899-03-6), Tricyclazole (41814-78-2), Mefenoxam (70630-17-0), Metalaxyl (57837-19-1), Acibenzolar (126448-41-7) (Acibenzolar-S-methyl (126448-41-7)), Mancozeb (8018-01-7), Ametoctradine (865318-97-4) Cyflufenamid (180409-60-3), and Kresoxim-methyl (143390-89-0). The compound of formula IIA is known from WO 2008/053044, the compound of formula IIIA is known from WO 2007/048556, the compound of formula IVA is known from WO 2010/000612.

Reference to the above components B includes reference to their salts and any usual derivatives, such as ester derivatives. In particular, reference to Acibenzolar includes reference to, and is preferably, Acibenzolar-S-methyl.

The combinations according to the invention may also comprise more than one of the active components B, if, for example, a broadening of the spectrum of pest control is desired. For instance, it may be advantageous in the agricultural practice to combine two or three components B with any of the compounds of formula I, or with any preferred member of the group of compounds of formula I. The mixtures of the invention may also comprise other active ingredients in addition to components A and B. In other embodiments the mixtures of the invention may include only components A and B as pesticidally active ingredients, e.g. no more than two pesticidally active ingredients.

Preferred substituents are, in any combination, as set out below.

$A^1$ and $A^2$ are preferably C—H.

$R^1$ is preferably hydrogen, cyano-$C_1$-$C_8$alkyl, $C_1$-$C_8$alkyl, $C_3$-$C_8$cycloalkyl, $C_3$-$C_8$cycloalkyl where one carbon atom in the cycloalkyl group is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_1$-$C_8$haloalkyl, $C_1$-$C_8$hydroxyalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^6$, 5-6 membered heteoaryl-$C_1$-$C_4$alkyl or 5-6 membered heteroaryl-$C_1$-$C_4$alkyl wherein the heteroaryl moiety is substituted by one to three $R^6$; more preferably $R^1$ is hydrogen, cyano-$C_1$-$C_8$alkyl-, $C_1$-$C_8$alkyl, $C_3$-$C_8$cycloalkyl, $C_3$-$C_8$cycloalkyl where one carbon atom in the cycloalkyl group is replaced by O, S, S(O) or $SO_2$, or $C_1$-$C_8$haloalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^6$, 5-6 membered heteroaryl-$C_1$-$C_4$alkyl or 5-6 membered heteroaryl-$C_1$-$C_4$alkyl wherein the heteroaryl moiety is substituted by one to three $R^6$; even more preferably $R^1$ is hydrogen, cyano-$C_1$-$C_6$alkyl, $C_1$-$C_6$alkyl, $C_3$-$C_6$cycloalkyl, $C_3$-$C_6$cycloalkyl where one carbon atom in the cycloalkyl group is replaced by O, S, S(O) or $SO_2$, or $C_1$-$C_6$haloalkyl, $C_1$-$C_6$hydroxyalkyl, $C_1$-$C_6$alkoxy-$C_1$-$C_6$alkyl, $C_2$-$C_6$alkenyl, $C_2$-$C_6$alkynyl, phenyl-$CH_2$-alkyl or phenyl-$CH_2$— wherein the phenyl moiety is substituted by one to three $R^6$, furanyl or furanyl substituted by one to three $R^6$, triazolyl or triazolyl optionally substituted by one to three $R^6$; yet even more preferably $R^1$ is hydrogen, $C_1$-$C_4$alkyl, $C_3$-$C_6$cycloalkyl, $C_1$-$C_4$haloalkyl, $C_1$-$C_4$hydroxyalkyl, $C_1$-$C_4$alkoxy-$C_1$-$C_4$alkyl, phenyl-$CH_2$-alkyl- or phenyl-$CH_2$— wherein the phenyl moiety is substituted by one to three $R^6$, furanyl or furanyl substituted by one to three $R^6$, thietanyl, oxetanyl, oxo-thietanyl, or dioxo-thietanyl; yet even more preferably $R^1$ is hydrogen, methyl, ethyl, propyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, cyanoethyl, benzyl, benzyl substituted by one to three $R^6$, or $R^1$ is pyridyl-methyl- or pyridyl-methyl-substituted by one to three $R^6$; yet even more preferably $R^1$ is methyl, ethyl, cyclopropyl, cyclobutyl, oxetanyl, thietanyl, trifluoroethyl, difluoroethyl, allyl, propargyl, cyanomethyl, cyanoethyl, benzyl, benzyl substituted by one to three $R^6$, or pyridine-methyl- or pyridine-methyl-substituted by one to three $R^6$, even more preferably methyl, ethyl, cyclopropyl, cyclobutyl, oxetanyl, thietanyl, trifluoroethyl, difluoroethyl, allyl, propargyl, cyanomethyl, cyanoethyl, benzyl, or pyridine-methyl-. Ethyl and trifluoroethyl are particularly preferred. Heteroaryl preferably refers to pyridyl, pyridazinyl, pyrimidinyl, pyrazinyl, pyrazolyl, furanyl, thiophenyl, oxazolyl, isoxazolyl or thiazolyl, more preferably pyridyl, pyrazolyl, furanyl, thiophenyl or thiazolyl, most preferably pyridyl.

$R^2$ is preferably trifluoromethyl.

Preferably each $R^3$ is independently chlorine or fluorine, most preferably chlorine.

$R^4$ is preferably chloro or methyl, more preferably methyl.

$R^5$ is preferably hydrogen.

Each $R^6$ is preferably independently halogen, cyano, $C_1$-$C_8$haloalkyl, $C_1$-$C_8$alkoxy or $C_1$-$C_8$haloalkoxy, most preferably fluoro, chloro, bromo, trifluoromethyl, trifluoromethoxy, cyano or methoxy.

p is preferably 2.

In one embodiment $A^1$ and $A^2$ are C—H; $R^2$ is trifluoromethyl, and $R^5$ is hydrogen.

In one embodiment $A^1$ and $A^2$ are C—H; $R^2$ is trifluoromethyl, $R^4$ is methyl, $R^5$ is hydrogen, each $R^3$ is chlorine, p is 2.

Compounds of formula I include at least one chiral centre and may exist as compounds of formula I* or compounds of formula I**.

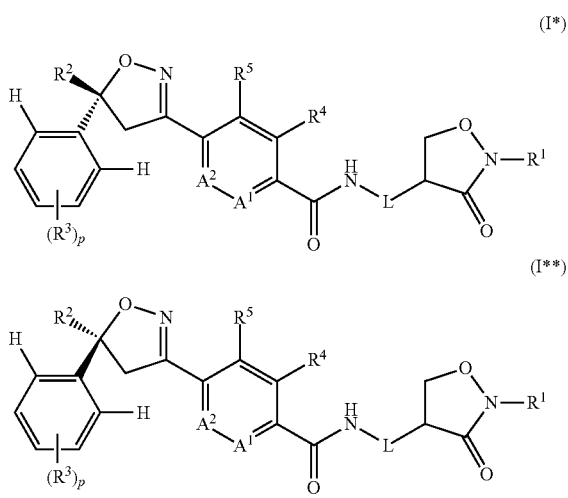

Compounds of formula I** are more biologically active than compounds of formula I*. Component A may be a mixture of compounds I* and I in any ratio e.g. in a molar ratio of 1:99 to 99:1, e.g. 10:1 to 1:10, e.g. a substantially 50:50 molar ratio. Preferably component A is a racemic mixture of the compounds of formula I and I* or is enantiomerically enriched for the compound of formula I. For example, when component A is an enantiomerically enriched mixture of formula I, the molar proportion of compound I compared to the total amount of both enantiomers (in component A and therefore the mixture of the invention per se) is for example greater than 50%, e.g. at least 55, 60, 65, 70, 75, 80, 85, 90, 95, 96, 97, 98, or at least 99%. In one embodiment component A is a compound of formula I in substantially pure form, e.g. it is provided substantially in the absence of the alternative enantiomer.

Preferred compounds of formula I are shown in the Tables below.

TABLE A

Compounds of formula (I-a)

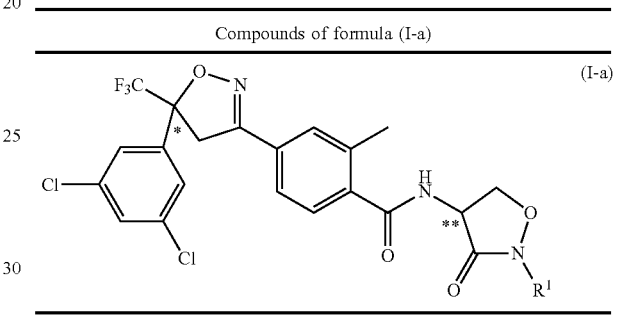

Table A provides 354 compounds and mixtures of formula (I-a) wherein $R^1$ has the values listed in table X below. The symbols * and ** indicate the location of the chiral centres.

TABLE B

Compounds of formula (I-b)

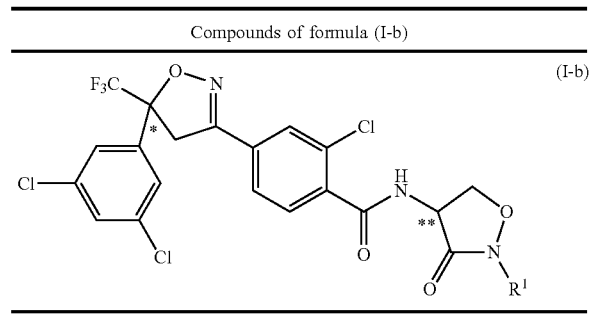

Table B provides 354 compounds and mixtures of formula (I-b) wherein $R^1$ has the values listed in table X below. The symbols * and ** indicate the location of the chiral centres.

TABLE C

Compounds of formula (I-c)

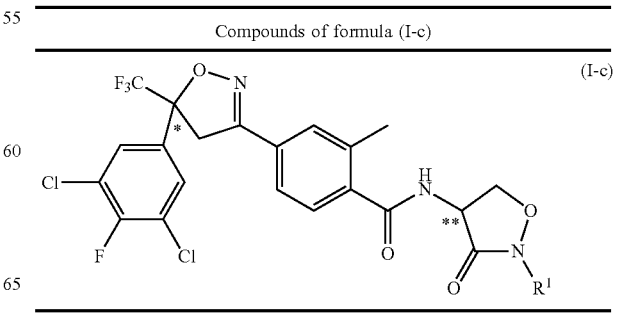

Table C provides 354 compounds and mixtures of formula (I-c) wherein R¹ has the values listed in table X below. The symbols * and ** indicate the location of the chiral centres.

TABLE D

Compounds of formula (I-d)

(I-d)

Table D provides 354 compounds and mixtures of formula (I-d) wherein R¹ has the values listed in table X below. The symbols * and ** indicate the location of the chiral centres.

TABLE E

Compounds of formula (I-e)

(I-e)

Table E provides 354 compounds and mixtures of formula (I-e) wherein R¹ has the values listed in table X below. The symbols * and ** indicate the location of the chiral centres.

TABLE F

Compounds of formula (I-f)

(I-f)

Table F provides 354 compounds and mixtures of formula (I-f) wherein R¹ has the values listed in table X below. The symbols * and ** indicate the location of the chiral centres.

Table X represents Table A when X is A, Table B when X is B, Table C when X is C, Table D when X is D, Table E when X is E, Table F when X is F.

| Compound numbers | Stereochemistry at* | Stereochemistry at** | R¹ |
|---|---|---|---|
| X.1 | Racemic mixture | Racemic mixture | ethyl- |
| X.2 | Racemic mixture | Racemic mixture | butyl- |
| X.3 | Racemic mixture | Racemic mixture | but-2-yl- |
| X.4 | Racemic mixture | Racemic mixture | 3-bromo-propyl- |
| X.5 | Racemic mixture | Racemic mixture | 2,2,2-trifluoro-ethyl- |
| X.6 | Racemic mixture | Racemic mixture | 3,3,3-trifluoro-propyl- |
| X.7 | Racemic mixture | Racemic mixture | 2-methoxy-ethyl- |
| X.8 | Racemic mixture | Racemic mixture | 1-methoxy-prop-2-yl- |
| X.9 | Racemic mixture | Racemic mixture | cyclobutyl- |
| X.10 | Racemic mixture | Racemic mixture | 2-methyl-cyclohex-1-yl- |
| X.11 | Racemic mixture | Racemic mixture | phenyl-methyl- |
| X.12 | Racemic mixture | Racemic mixture | 1-phenyl-eth-1-yl- |
| X.13 | Racemic mixture | Racemic mixture | 2-phenyl-eth-1-yl- |
| X.14 | Racemic mixture | Racemic mixture | (3-chloro-phenyl)-methyl- |
| X.15 | Racemic mixture | Racemic mixture | (2-fluoro-phenyl)-methyl- |
| X.16 | Racemic mixture | Racemic mixture | (4-methoxy-phenyl)-methyl- |
| X.17 | Racemic mixture | Racemic mixture | (2-trifluoromethyl-phenyl)-methyl- |
| X.18 | Racemic mixture | Racemic mixture | (2-trifluoromethoxy-phenyl)-methyl- |
| X.19 | Racemic mixture | Racemic mixture | (pyrid-2-yl)-methyl- |
| X.20 | Racemic mixture | Racemic mixture | (pyrid-3-yl)-methyl- |
| X.21 | Racemic mixture | Racemic mixture | (2-chloro-pyrid-5-yl)-methyl- |
| X.22 | Racemic mixture | Racemic mixture | (1-methyl-1H-imidazol-4-yl)-methyl- |
| X.23 | Racemic mixture | Racemic mixture | (furan-2-yl)-methyl- |
| X.24 | Racemic mixture | Racemic mixture | 2-(thiophen-2'-yl)-eth-1-yl- |
| X.25 | Racemic mixture | Racemic mixture | 2-(indol-3'-yl)-eth-1-yl- |
| X.26 | Racemic mixture | Racemic mixture | (1H-benzimidazol-2-yl)-methyl- |
| X.27 | Racemic mixture | Racemic mixture | (oxetan-2-yl)-methyl- |
| X.28 | Racemic mixture | Racemic mixture | (tetrahydrofuran-2-yl)-methyl- |
| X.29 | Racemic mixture | Racemic mixture | 2-([1',3']dioxolan-2'-yl)-eth-1-yl- |
| X.30 | Racemic mixture | Racemic mixture | 2-(morpholin-4'-yl)-eth-1-yl- |
| X.31 | Racemic mixture | Racemic mixture | 2-(benzo[1',3']dioxol-5'-yl)-eth-1-yl- |
| X.32 | Racemic mixture | Racemic mixture | (2,3-dihydro-benzo[1,4]dioxin-6-yl)-methyl- |
| X.33 | Racemic mixture | Racemic mixture | 2-chloro-phenyl- |
| X.34 | Racemic mixture | Racemic mixture | 3-fluoro-phenyl- |
| X.35 | Racemic mixture | Racemic mixture | 2-methyl-phenyl- |
| X.36 | Racemic mixture | Racemic mixture | 2-chloro-6-methyl-phenyl- |
| X.37 | Racemic mixture | Racemic mixture | 2-trifluoromethyl-phenyl- |
| X.38 | Racemic mixture | Racemic mixture | 2,4-dimethoxy-phenyl- |
| X.39 | Racemic mixture | Racemic mixture | 3-methyl-pyrid-2-yl- |
| X.40 | Racemic mixture | Racemic mixture | 1,3-dimethyl-1H-pyrazol-5-yl- |
| X.41 | Racemic mixture | Racemic mixture | 4-methyl-thiazol-2-yl- |
| X.42 | Racemic mixture | Racemic mixture | 5-methyl-thiadiazol-2-yl- |
| X.43 | Racemic mixture | Racemic mixture | quinolin-2-yl- |
| X.44 | Racemic mixture | Racemic mixture | quinolin-5-yl- |
| X.45 | Racemic mixture | Racemic mixture | benzothiazol-6-yl- |
| X.46 | Racemic mixture | Racemic mixture | 4-methyl-benzothiazol-2-yl- |
| X.47 | Racemic mixture | Racemic mixture | thietan-3-yl- |
| X.48 | Racemic mixture | Racemic mixture | 1-oxo-thietan-3-yl- |
| X.49 | Racemic mixture | Racemic mixture | 1,1-dioxo-thietan-3-yl- |
| X.50 | Racemic mixture | Racemic mixture | 3-methyl-thietan-3-yl- |
| X.51 | Racemic mixture | Racemic mixture | oxetan-3yl |
| X.52 | Racemic mixture | Racemic mixture | tetrahydropyran-4-yl |
| X.53 | Racemic mixture | Racemic mixture | hydrogen |
| X.54 | Racemic mixture | Racemic mixture | methyl |
| X.55 | Racemic mixture | Racemic mixture | propyl |
| X.56 | Racemic mixture | Racemic mixture | 2,2-difluoro-ethyl- |
| X.57 | Racemic mixture | Racemic mixture | 2-fluoro-ethyl- |
| X.58 | S | Racemic mixture | ethyl- |
| X.59 | S | Racemic mixture | butyl- |
| X.60 | S | Racemic mixture | but-2-yl- |
| X.61 | S | Racemic mixture | 3-bromo-propyl- |

-continued

| Compound numbers | Stereochemistry at* | Stereochemistry at** | R¹ |
|---|---|---|---|
| X.62 | S | Racemic mixture | 2,2,2-trifluoro-ethyl- |
| X.63 | S | Racemic mixture | 3,3,3-trifluoro-propyl- |
| X.64 | S | Racemic mixture | 2-methoxy-ethyl- |
| X.65 | S | Racemic mixture | 1-methoxy-prop-2-yl- |
| X.66 | S | Racemic mixture | cyclobutyl- |
| X.67 | S | Racemic mixture | 2-methyl-cyclohex-1-yl- |
| X.68 | S | Racemic mixture | phenyl-methyl- |
| X.69 | S | Racemic mixture | 1-phenyl-eth-1-yl- |
| X.70 | S | Racemic mixture | 2-phenyl-eth-1-yl- |
| X.71 | S | Racemic mixture | (3-chloro-phenyl)-methyl- |
| X.72 | S | Racemic mixture | (2-fluoro-phenyl)-methyl- |
| X.73 | S | Racemic mixture | (4-methoxy-phenyl)-methyl- |
| X.74 | S | Racemic mixture | (2-trifluoromethyl-phenyl)-methyl- |
| X.75 | S | Racemic mixture | (2-trifluoromethoxy-phenyl)-methyl- |
| X.76 | S | Racemic mixture | (pyrid-2-yl)-methyl- |
| X.77 | S | Racemic mixture | (pyrid-3-yl)-methyl- |
| X.78 | S | Racemic mixture | (2-chloro-pyrid-5-yl)-methyl- |
| X.79 | S | Racemic mixture | (1-methyl-1H-imidazol-4-yl)-methyl- |
| X.80 | S | Racemic mixture | (furan-2-yl)-methyl- |
| X.81 | S | Racemic mixture | 2-(thiophen-2'-yl)-eth-1-yl- |
| X.82 | S | Racemic mixture | 2-(indol-3'-yl)-eth-1-yl- |
| X.83 | S | Racemic mixture | (1H-benzimidazol-2-yl)-methyl- |
| X.84 | S | Racemic mixture | (oxetan-2-yl)-methyl- |
| X.85 | S | Racemic mixture | (tetrahydrofuran-2-yl)-methyl- |
| X.86 | S | Racemic mixture | 2-([1',3']dioxolan-2'-yl)-eth-1-yl- |
| X.87 | S | Racemic mixture | 2-(morpholin-4'-yl)-eth-1-yl- |
| X.88 | S | Racemic mixture | 2-(benzo[1',3']dioxol-5'-yl)-eth-1-yl- |
| X.89 | S | Racemic mixture | (2,3-dihydro-benzo[1,4]dioxin-6-yl)-methyl- |
| X.90 | S | Racemic mixture | 2-chloro-phenyl- |
| X.91 | S | Racemic mixture | 3-fluoro-phenyl- |
| X.92 | S | Racemic mixture | 2-methyl-phenyl- |
| X.93 | S | Racemic mixture | 2-chloro-6-methyl-phenyl- |
| X.94 | S | Racemic mixture | 2-trifluoromethyl-phenyl- |
| X.95 | S | Racemic mixture | 2,4-dimethoxy-phenyl- |
| X.96 | S | Racemic mixture | 3-methyl-pyrid-2-yl- |
| X.97 | S | Racemic mixture | 1,3-dimethyl-1H-pyrazol-5-yl- |
| X.98 | S | Racemic mixture | 4-methyl-thiazol-2-yl- |
| X.99 | S | Racemic mixture | 5-methyl-thiadiazol-2-yl- |
| X.100 | S | Racemic mixture | quinolin-2-yl- |
| X.101 | S | Racemic mixture | quinolin-5-yl- |
| X.102 | S | Racemic mixture | benzothiazol-6-yl- |
| X.103 | S | Racemic mixture | 4-methyl-benzothiazol-2-yl- |
| X.104 | S | Racemic mixture | thietan-3-yl- |
| X.105 | S | Racemic mixture | 1-oxo-thietan-3-yl- |
| X.106 | S | Racemic mixture | 1,1-dioxo-thietan-3-yl- |
| X.107 | S | Racemic mixture | 3-methyl-thietan-3-yl- |
| X.108 | S | Racemic mixture | oxetan-3yl |
| X.109 | S | Racemic mixture | tetrahydropyran-4-yl |
| X.110 | S | Racemic mixture | hydrogen |
| X.111 | S | Racemic mixture | methyl |
| X.112 | S | Racemic mixture | propyl |
| X.113 | S | Racemic mixture | 2,2-difluoro-ethyl- |
| X.114 | S | Racemic mixture | 2-fluoro-ethyl- |
| X.115 | Racemic mixture | Racemic mixture | isopropyl |
| X.116 | Racemic mixture | Racemic mixture | cyclopropyl |
| X.117 | S | Racemic mixture | isopropyl |
| X.118 | S | Racemic mixture | cyclopropyl |
| X.119 | Racemic mixture | S | ethyl- |
| X.120 | Racemic mixture | S | butyl- |
| X.121 | Racemic mixture | S | but-2-yl- |
| X.122 | Racemic mixture | S | 3-bromo-propyl- |
| X.123 | Racemic mixture | S | 2,2,2-trifluoro-ethyl- |
| X.124 | Racemic mixture | S | 3,3,3-trifluoro-propyl- |
| X.125 | Racemic mixture | S | 2-methoxy-ethyl- |
| X.126 | Racemic mixture | S | 1-methoxy-prop-2-yl- |
| X.127 | Racemic mixture | S | cyclobutyl- |
| X.128 | Racemic mixture | S | 2-methyl-cyclohex-1-yl- |
| X.129 | Racemic mixture | S | phenyl-methyl- |
| X.130 | Racemic mixture | S | 1-phenyl-eth-1-yl- |
| X.131 | Racemic mixture | S | 2-phenyl-eth-1-yl- |
| X.132 | Racemic mixture | S | (3-chloro-phenyl)-methyl- |
| X.133 | Racemic mixture | S | (2-fluoro-phenyl)-methyl- |
| X.134 | Racemic mixture | S | (4-methoxy-phenyl)-methyl- |
| X.135 | Racemic mixture | S | (2-trifluoromethyl-phenyl)-methyl- |
| X.136 | Racemic mixture | S | (2-trifluoromethoxy-phenyl)-methyl- |
| X.137 | Racemic mixture | S | (pyrid-2-yl)-methyl- |
| X.138 | Racemic mixture | S | (pyrid-3-yl)-methyl- |
| X.139 | Racemic mixture | S | (2-chloro-pyrid-5-yl)-methyl- |
| X.140 | Racemic mixture | S | (1-methyl-1H-imidazol-4-yl)-methyl- |
| X.141 | Racemic mixture | S | (furan-2-yl)-methyl- |
| X.142 | Racemic mixture | S | 2-(thiophen-2'-yl)-eth-1-yl- |
| X.143 | Racemic mixture | S | 2-(indol-3'-yl)-eth-1-yl- |
| X.144 | Racemic mixture | S | (1H-benzimidazol-2-yl)-methyl- |
| X.145 | Racemic mixture | S | (oxetan-2-yl)-methyl- |
| X.146 | Racemic mixture | S | (tetrahydrofuran-2-yl)-methyl- |
| X.147 | Racemic mixture | S | 2-([1',3']dioxolan-2'-yl)-eth-1-yl- |
| X.148 | Racemic mixture | S | 2-(morpholin-4'-yl)-eth-1-yl- |
| X.149 | Racemic mixture | S | 2-(benzo[1',3']dioxol-5'-yl)-eth-1-yl- |
| X.150 | Racemic mixture | S | (2,3-dihydro-benzo[1,4]dioxin-6-yl)-methyl- |
| X.151 | Racemic mixture | S | 2-chloro-phenyl- |
| X.152 | Racemic mixture | S | 3-fluoro-phenyl- |
| X.153 | Racemic mixture | S | 2-methyl-phenyl- |
| X.154 | Racemic mixture | S | 2-chloro-6-methyl-phenyl- |
| X.155 | Racemic mixture | S | 2-trifluoromethyl-phenyl- |
| X.156 | Racemic mixture | S | 2,4-dimethoxy-phenyl- |
| X.157 | Racemic mixture | S | 3-methyl-pyrid-2-yl- |
| X.158 | Racemic mixture | S | 1,3-dimethyl-1H-pyrazol-5-yl- |
| X.159 | Racemic mixture | S | 4-methyl-thiazol-2-yl- |
| X.160 | Racemic mixture | S | 5-methyl-thiadiazol-2-yl- |
| X.161 | Racemic mixture | S | quinolin-2-yl- |
| X.162 | Racemic mixture | S | quinolin-5-yl- |
| X.163 | Racemic mixture | S | benzothiazol-6-yl- |
| X.164 | Racemic mixture | S | 4-methyl-benzothiazol-2-yl- |
| X.165 | Racemic mixture | S | thietan-3-yl- |
| X.166 | Racemic mixture | S | 1-oxo-thietan-3-yl- |
| X.167 | Racemic mixture | S | 1,1-dioxo-thietan-3-yl- |
| X.168 | Racemic mixture | S | 3-methyl-thietan-3-yl- |
| X.169 | Racemic mixture | S | oxetan-3yl |
| X.170 | Racemic mixture | S | tetrahydropyran-4-yl |
| X.171 | Racemic mixture | S | hydrogen |
| X.172 | Racemic mixture | S | methyl |
| X.173 | Racemic mixture | S | propyl |
| X.174 | Racemic mixture | S | 2,2-difluoro-ethyl- |
| X.175 | Racemic mixture | S | 2-fluoro-ethyl- |
| X.176 | S | S | ethyl- |
| X.177 | S | S | butyl- |
| X.178 | S | S | but-2-yl- |
| X.179 | S | S | 3-bromo-propyl- |
| X.180 | S | S | 2,2,2-trifluoro-ethyl- |
| X.181 | S | S | 3,3,3-trifluoro-propyl- |

-continued

| Compound numbers | Stereochemistry at* | Stereochemistry at** | R¹ |
|---|---|---|---|
| X.182 | S | S | 2-methoxy-ethyl- |
| X.183 | S | S | 1-methoxy-prop-2-yl- |
| X.184 | S | S | cyclobutyl- |
| X.185 | S | S | 2-methyl-cyclohex-1-yl- |
| X.186 | S | S | phenyl-methyl- |
| X.187 | S | S | 1-phenyl-eth-1-yl- |
| X.188 | S | S | 2-phenyl-eth-1-yl- |
| X.189 | S | S | (3-chloro-phenyl)-methyl- |
| X.190 | S | S | (2-fluoro-phenyl)-methyl- |
| X.191 | S | S | (4-methoxy-phenyl)-methyl- |
| X.192 | S | S | (2-trifluoromethyl-phenyl)-methyl- |
| X.193 | S | S | (2-trifluoromethoxy-phenyl)-methyl- |
| X.194 | S | S | (pyrid-2-yl)-methyl- |
| X.195 | S | S | (pyrid-3-yl)-methyl- |
| X.196 | S | S | (2-chloro-pyrid-5-yl)-methyl- |
| X.197 | S | S | (1-methyl-1H-imidazol-4-yl)-methyl- |
| X.198 | S | S | (furan-2-yl)-methyl- |
| X.199 | S | S | 2-(thiophen-2'-yl)-eth-1-yl- |
| X.200 | S | S | 2-(indol-3'-yl)-eth-1-yl- |
| X.201 | S | S | (1H-benzimidazol-2-yl)-methyl- |
| X.202 | S | S | (oxetan-2-yl)-methyl- |
| X.203 | S | S | (tetrahydrofuran-2-yl)-methyl- |
| X.204 | S | S | 2-([1',3']dioxolan-2'-yl)-eth-1-yl- |
| X.205 | S | S | 2-(morpholin-4'-yl)-eth-1-yl- |
| X.206 | S | S | 2-(benzo[1',3']dioxol-5'-yl)-eth-1-yl- |
| X.207 | S | S | (2,3-dihydro-benzo[1,4]dioxin-6-yl)-methyl- |
| X.208 | S | S | 2-chloro-phenyl- |
| X.209 | S | S | 3-fluoro-phenyl- |
| X.210 | S | S | 2-methyl-phenyl- |
| X.211 | S | S | 2-chloro-6-methyl-phenyl- |
| X.212 | S | S | 2-trifluoromethyl-phenyl- |
| X.213 | S | S | 2,4-dimethoxy-phenyl- |
| X.214 | S | S | 3-methyl-pyrid-2-yl- |
| X.215 | S | S | 1,3-dimethyl-1H-pyrazol-5-yl- |
| X.216 | S | S | 4-methyl-thiazol-2-yl- |
| X.217 | S | S | 5-methyl-thiadiazol-2-yl- |
| X.218 | S | S | quinolin-2-yl- |
| X.219 | S | S | quinolin-5-yl- |
| X.220 | S | S | benzothiazol-6-yl- |
| X.221 | S | S | 4-methyl-benzothiazol-2-yl- |
| X.222 | S | S | thietan-3-yl- |
| X.223 | S | S | 1-oxo-thietan-3-yl- |
| X.224 | S | S | 1,1-dioxo-thietan-3-yl- |
| X.225 | S | S | 3-methyl-thietan-3-yl- |
| X.226 | S | S | oxetan-3yl |
| X.227 | S | S | tetrahydropyran-4-yl |
| X.228 | S | S | hydrogen |
| X.229 | S | S | methyl |
| X.230 | S | S | propyl |
| X.231 | S | S | 2,2-difluoro-ethyl- |
| X.232 | S | S | 2-fluoro-ethyl- |
| X.233 | Racemic mixture | S | isopropyl |
| X.234 | Racemic mixture | S | cyclopropyl |
| X.235 | S | S | isopropyl |
| X.236 | S | S | cyclopropyl |
| X.237 | Racemic mixture | R | ethyl- |
| X.238 | Racemic mixture | R | butyl- |
| X.239 | Racemic mixture | R | but-2-yl- |
| X.240 | Racemic mixture | R | 3-bromo-propyl- |
| X.241 | Racemic mixture | R | 2,2,2-trifluoro-ethyl- |
| X.242 | Racemic mixture | R | 3,3,3-trifluoro-propyl- |
| X.243 | Racemic mixture | R | 2-methoxy-ethyl- |
| X.244 | Racemic mixture | R | 1-methoxy-prop-2-yl- |
| X.245 | Racemic mixture | R | cyclobutyl- |
| X.246 | Racemic mixture | R | 2-methyl-cyclohex-1-yl- |
| X.247 | Racemic mixture | R | phenyl-methyl- |
| X.248 | Racemic mixture | R | 1-phenyl-eth-1-yl- |
| X.249 | Racemic mixture | R | 2-phenyl-eth-1-yl- |
| X.250 | Racemic mixture | R | (3-chloro-phenyl)-methyl- |
| X.251 | Racemic mixture | R | (2-fluoro-phenyl)-methyl- |
| X.252 | Racemic mixture | R | (4-methoxy-phenyl)-methyl- |
| X.253 | Racemic mixture | R | (2-trifluoromethyl-phenyl)-methyl- |
| X.254 | Racemic mixture | R | (2-trifluoromethoxy-phenyl)-methyl- |
| X.255 | Racemic mixture | R | (pyrid-2-yl)-methyl- |
| X.256 | Racemic mixture | R | (pyrid-3-yl)-methyl- |
| X.257 | Racemic mixture | R | (2-chloro-pyrid-5-yl)-methyl- |
| X.258 | Racemic mixture | R | (1-methyl-1H-imidazol-4-yl)-methyl- |
| X.259 | Racemic mixture | R | (furan-2-yl)-methyl- |
| X.260 | Racemic mixture | R | 2-(thiophen-2'-yl)-eth-1-yl- |
| X.261 | Racemic mixture | R | 2-(indol-3'-yl)-eth-1-yl- |
| X.262 | Racemic mixture | R | (1H-benzimidazol-2-yl)-methyl- |
| X.263 | Racemic mixture | R | (oxetan-2-yl)-methyl- |
| X.264 | Racemic mixture | R | (tetrahydrofuran-2-yl)-methyl- |
| X.265 | Racemic mixture | R | 2-([1',3']dioxolan-2'-yl)-eth-1-yl- |
| X.266 | Racemic mixture | R | 2-(morpholin-4'-yl)-eth-1-yl- |
| X.267 | Racemic mixture | R | 2-(benzo[1',3']dioxol-5'-yl)-eth-1-yl- |
| X.268 | Racemic mixture | R | (2,3-dihydro-benzo[1,4]dioxin-6-yl)-methyl- |
| X.269 | Racemic mixture | R | 2-chloro-phenyl- |
| X.270 | Racemic mixture | R | 3-fluoro-phenyl- |
| X.271 | Racemic mixture | R | 2-methyl-phenyl- |
| X.272 | Racemic mixture | R | 2-chloro-6-methyl-phenyl- |
| X.273 | Racemic mixture | R | 2-trifluoromethyl-phenyl- |
| X.274 | Racemic mixture | R | 2,4-dimethoxy-phenyl- |
| X.275 | Racemic mixture | R | 3-methyl-pyrid-2-yl- |
| X.276 | Racemic mixture | R | 1,3-dimethyl-1H-pyrazol-5-yl- |
| X.277 | Racemic mixture | R | 4-methyl-thiazol-2-yl- |
| X.278 | Racemic mixture | R | 5-methyl-thiadiazol-2-yl- |
| X.279 | Racemic mixture | R | quinolin-2-yl- |
| X.280 | Racemic mixture | R | quinolin-5-yl- |
| X.281 | Racemic mixture | R | benzothiazol-6-yl- |
| X.282 | Racemic mixture | R | 4-methyl-benzothiazol-2-yl- |
| X.283 | Racemic mixture | R | thietan-3-yl- |
| X.284 | Racemic mixture | R | 1-oxo-thietan-3-yl- |
| X.285 | Racemic mixture | R | 1,1-dioxo-thietan-3-yl- |
| X.286 | Racemic mixture | R | 3-methyl-thietan-3-yl- |
| X.287 | Racemic mixture | R | oxetan-3yl |
| X.288 | Racemic mixture | R | tetrahydropyran-4-yl |
| X.289 | Racemic mixture | R | hydrogen |
| X.290 | Racemic mixture | R | methyl |
| X.291 | Racemic mixture | R | propyl |
| X.292 | Racemic mixture | R | 2,2-difluoro-ethyl- |
| X.293 | Racemic mixture | R | 2-fluoro-ethyl- |
| X.294 | S | R | ethyl- |
| X.295 | S | R | butyl- |
| X.296 | S | R | but-2-yl- |
| X.297 | S | R | 3-bromo-propyl- |
| X.298 | S | R | 2,2,2-trifluoro-ethyl- |
| X.299 | S | R | 3,3,3-trifluoro-propyl- |
| X.300 | S | R | 2-methoxy-ethyl- |
| X.301 | S | R | 1-methoxy-prop-2-yl- |

-continued

| Compound numbers | Stereochemistry at* | Stereochemistry at** | R¹ |
|---|---|---|---|
| X.302 | S | R | cyclobutyl- |
| X.303 | S | R | 2-methyl-cyclohex-1-yl- |
| X.304 | S | R | phenyl-methyl- |
| X.305 | S | R | 1-phenyl-eth-1-yl- |
| X.306 | S | R | 2-phenyl-eth-1-yl- |
| X.307 | S | R | (3-chloro-phenyl)-methyl- |
| X.308 | S | R | (2-fluoro-phenyl)-methyl- |
| X.309 | S | R | (4-methoxy-phenyl)-methyl- |
| X.310 | S | R | (2-trifluoromethyl-phenyl)-methyl- |
| X.311 | S | R | (2-trifluoromethoxy-phenyl)-methyl- |
| X.312 | S | R | (pyrid-2-yl)-methyl- |
| X.313 | S | R | (pyrid-3-yl)-methyl- |
| X.314 | S | R | (2-chloro-pyrid-5-yl)-methyl- |
| X.315 | S | R | (1-methyl-1H-imidazol-4-yl)-methyl- |
| X.316 | S | R | (furan-2-yl)-methyl- |
| X.317 | S | R | 2-(thiophen-2'-yl)-eth-1-yl- |
| X.318 | S | R | 2-(indol-3'-yl)-eth-1-yl- |
| X.319 | S | R | (1H-benzimidazol-2-yl)-methyl- |
| X.320 | S | R | (oxetan-2-yl)-methyl- |
| X.321 | S | R | (tetrahydrofuran-2-yl)-methyl- |
| X.322 | S | R | 2-([1',3']dioxolan-2'-yl)-eth-1-yl- |
| X.323 | S | R | 2-(morpholin-4'-yl)-eth-1-yl- |
| X.324 | S | R | 2-(benzo[1'3']dioxol-5'-yl)-eth-1-yl- |
| X.325 | S | R | (2,3-dihydro-benzo[1,4]dioxin-6-yl)-methyl- |
| X.326 | S | R | 2-chloro-phenyl- |
| X.327 | S | R | 3-fluoro-phenyl- |
| X.328 | S | R | 2-methyl-phenyl- |
| X.329 | S | R | 2-chloro-6-methyl-phenyl- |
| X.330 | S | R | 2-trifluoromethyl-phenyl- |
| X.331 | S | R | 2,4-dimethoxy-phenyl- |
| X.332 | S | R | 3-methyl-pyrid-2-yl- |
| X.333 | S | R | 1,3-dimethyl-1H-pyrazol-5-yl- |
| X.334 | S | R | 4-methyl-thiazol-2-yl- |
| X.335 | S | R | 5-methyl-thiadiazol-2-yl- |
| X.336 | S | R | quinolin-2-yl- |
| X.337 | S | R | quinolin-5-yl- |
| X.338 | S | R | benzothiazol-6-yl- |
| X.339 | S | R | 4-methyl-benzothiazol-2-yl- |
| X.340 | S | R | thietan-3-yl- |
| X.341 | S | R | 1-oxo-thietan-3-yl- |
| X.342 | S | R | 1,1-dioxo-thietan-3-yl- |
| X.343 | S | R | 3-methyl-thietan-3-yl- |
| X.344 | S | R | oxetan-3yl |
| X.345 | S | R | tetrahydropyran-4-yl |
| X.346 | S | R | hydrogen |
| X.347 | S | R | methyl |
| X.348 | S | R | propyl |
| X.349 | S | R | 2,2-difluoro-ethyl- |
| X.350 | S | R | 2-fluoro-ethyl- |
| X.351 | Racemic mixture | R | isopropyl |
| X.352 | Racemic mixture | R | cyclopropyl |
| X.353 | S | R | isopropyl |
| X.354 | S | R | cyclopropyl |

The present invention includes all isomers of compounds of formula (I), salts and N-oxides thereof, including enantiomers, diastereomers and tautomers. Component A may be a mixture of any type of isomer of a compound of formula I, or may be substantially a single type of isomer.

In one embodiment of the invention component B is a compound selected from the group consisting of Azoxystrobin, Isopyrazam, Chlorothalonil, Cyproconazole, Difenoconaozle, Mandipropamid, Mefenoxam, Metalaxyl, Sedaxane, Acibenzolar (including Acibenzolar-S-methyl), Fludioxonil, Cyprodinil, Penconazole, Propiconazole, Mancozeb, Prothioconazole, Pyraclostrobin, Boscalid, Bixafen, Fluopyram, Penthiopyrad, Thiabendazole, Fluazinam, Fenpropidin, Cyclufenamid, Tebuconaozle, Trifoxystrobin, Fluxapyroxad, Penflufen, Fluoxastrobin, Kresoxim-methyl, Benthiavalicarb, Dimethomorph, a compound of formula IIA, a compound of formula IIIA and a compound of formula IVA.

In one embodiment component B is a compound selected from the group consisting of Azoxystrobin, Isopyrazam, Chlorothalonil, Cyroconazole, Difenoconaozle, Mandipropamid, Mefenoxam, Metalaxyl, Sedaxane, Acibenzolar (including Acibenzolar-S-methyl), Fludioxonil, Cyprodinil, Penconazole, Propiconazole, Mancozeb, Prothioconazole, Pyraclostrobin, Boscalid, Bixafen, Fluopyram, Penthiopyrad, Thiabendazole, a compound of formula III and a compound of formula IV.

In one embodiment component B is a compound selected from the group consisting of Azoxystrobin, Isopyrazam, Chlorothalonil, Cyroconazole, Difenoconaozle, Mandipropamid, Mefenoxam, Metalaxyl, Sedaxane, Acibenzolar (including Acibenzolar-S-methyl), Fludioxonil, Thiabendazole, a compound of formula IIIA and a compound of formula IV. More preferably component B is a compound selected from the group consisting of Azoxystrobin, Isopyrazam, Chlorothalonil, Cyproconazole, Difenoconaozle, Mandipropamid, Mefenoxam, a compound of formula IIIA and a compound of formula IVA.

In one embodiment component B is a strobilurin fungicide including those selected from the group consisting of: Azoxystrobin, Dimoxystrobin, Enestrobin, Fluoxastrobin, Kresoxim-methyl, Metominostrobin, Orysastrobin, Picoxystrobin, Pyraclostrobin and Trifloxystrobin; or an azole fungicide including those selected from the group consisting of:

Azaconazole, Bromuconazole, Cyproconazole, Difenoconazole, Diniconazole, Diniconazole-M, Epoxiconazole, Fenbuconazole, Fluquinconazole, Flusilazole, Flutriafol, Hexaconazole, Imazalil, Imibenconazole, Ipconazole, Metconazole, Myclobutanil, Oxpoconazole, Pefurazoate, Penconazole, Prochloraz, Propiconazole, Prothioconazole, Simeconazole, Tebuconazole, Tetraconazole, Triadimefon, Triadimenol, Triflumizole, Triticonazole, Diclobutrazol, Etaconazole, Furconazole, Furconazole-cis, Thiabendazole and Quinconazole; or a carboxamide fungicide including those selected from the group consisting of:

Isopyrazam, Sedaxane, Bixafen, Penthiopyrad, Fluxapyroxad, Boscalid, Penflufen, Fluopyram, a compound of formula IIA, a compound of formula IIIA and a compound of formula IVA.

Where compound B is an azole, triazoles are preferred.

In one embodiment component B is a Azoxystrobin, cyproconazole or a compound of formula III.

The invention also relates to the following combinations:
A mixture of a compound of formula I selected from Tables A, B, C, D, E and F+Azoxystrobin.
A mixture of a compound of formula I selected from Tables A, B, C, D, E and F+Isopyrazam.
A mixture of a compound of formula I selected from Tables A, B, C, D, E and F+Chlorothalonil.

A mixture of a compound of formula I selected from Tables A, B, C, D, E and F+Cyproconazole.
A mixture of a compound of formula I selected from Tables A, B, C, D, E and F+Difenoconaozle.
A mixture of a compound of formula I selected from Tables A, B, C, D, E and F+Mandipropamid.
A mixture of a compound of formula I selected from Tables A, B, C, D, E and F+Mefenoxam.
A mixture of a compound of formula I selected from Tables A, B, C, D, E and F+Metalaxyl.
A mixture of a compound of formula I selected from Tables A, B, C, D, E and F+Sedaxane.
A mixture of a compound of formula I selected from Tables A, B, C, D, E and F+Acibenzolar.
A mixture of a compound of formula I selected from Tables A, B, C, D, E and F+Acibenzolar-S-Methyl.
A mixture of a compound of formula I selected from Tables A, B, C, D, E and F+a compound of formula IIA.
A mixture of a compound of formula I selected from Tables A, B, C, D, E and F+a compound of formula IIIA.
A mixture of a compound of formula I selected from Tables A, B, C, D, E and F+a compound of formula IVA.
A mixture of a compound of formula I selected from Tables A, B, C, D, E and F+Fludioxonil.
A mixture of a compound of formula I selected from Tables A, B, C, D, E and F+Cyprodinil.
A mixture of a compound of formula I selected from Tables A, B, C, D, E and F+Penconazole.
A mixture of a compound of formula I selected from Tables A, B, C, D, E and F+Propiconazole.
A mixture of a compound of formula I selected from Tables A, B, C, D, E and F+Mancozeb.
A mixture of a compound of formula I selected from Tables A, B, C, D, E and F+Prothioconazole.
A mixture of a compound of formula I selected from Tables A, B, C, D, E and F+Pyraclostrobin.
A mixture of a compound of formula I selected from Tables A, B, C, D, E and F+Boscalid.
A mixture of a compound of formula I selected from Tables A, B, C, D, E and F+Bixafen.
A mixture of a compound of formula I selected from Tables A, B, C, D, E and F+Fluopyram.
A mixture of a compound of formula I selected from Tables A, B, C, D, E and F+Penthiopyrad.
A mixture of a compound of formula I selected from Tables A, B, C, D, E and F+Thiabendazole.
A mixture of a compound of formula I selected from Tables A, B, C, D, E and F+Fluazinam.
A mixture of a compound of formula I selected from Tables A, B, C, D, E and F+Fenpropidin.
A mixture of a compound of formula I selected from Tables A, B, C, D, E and F+Cyclufenamid.
A mixture of a compound of formula I selected from Tables A, B, C, D, E and F+Tebuconaozle.
A mixture of a compound of formula I selected from Tables A, B, C, D, E and F+Trifoxystrobin.
A mixture of a compound of formula I selected from Tables A, B, C, D, E and F+Fluoxastrobin.
A mixture of a compound of formula I selected from Tables A, B, C, D, E and F+Kresoxim-methyl.
A mixture of a compound of formula I selected from Tables A, B, C, D, E and F+Benthiavalicarb.
A mixture of a compound of formula I selected from Tables A, B, C, D, E and F+Dimethomorph.
A mixture of a compound of formula I selected from Tables A, B, C, D, E and F+Ametoctradine.
A mixture of a compound of formula I selected from Tables A, B, C, D, E and F+Fluxapyroxad.
A mixture of a compound of formula I selected from Tables A, B, C, D, E and F+Penflufen.

In one embodiment the ratio of formula I to azoxystrobin by weight in the composition may be 1:1.5 to 1:10. Examples of ratios falling within this range include 1:2, 1:3, 1:4, 1:5, 1:6, 1:7, 1:8, 1:9. In another embodiment the ratio of formula I to azoxystrobin may be 4000:1 or less, e.g. 1000:1 or less, e.g. 100:1 or less. For example the ratio of the compound of formula I to azoxystrobin is e.g. 1:250 to 250:1, e.g. 1:100 to 100:1, e.g. 100:1 to 1:10, e.g. 100:1 to 1:1, e.g. 50:1 to 1:1.

In one embodiment the ratio of the compound of formula I to isopyrazam by weight in the composition may be 1:1 to 1:3. Examples of ratios falling within this range include 1:1.5, 1:2, 1:2.5. In another embodiment the ratio of formula I to isopyazam may be 4000:1 or less, e.g. 1000:1 or less, e.g. 100:1 or less. For example the ratio of the compound of formula I to isopyazam is e.g. 1:250 to 250:1, e.g. 1:100 to 100:1, e.g. 100:1 to 1:10, e.g. 100:1 to 1:1, e.g. 50:1 to 1:1.

In one embodiment ratio of the compound of formula I to chlorothalonil by weight in the composition may be 1:5 to 1:50. Examples of ratios falling within this range include 1:10, 1:15, 1:20, 1:25, 1:30, 1:35, 1:40, 1:45. In another embodiment the ratio of formula I to chlorothalonil may be 4000:1 or less, e.g. 1000:1 or less, e.g. 100:1 or less. For example the ratio of the compound of formula I to chlorothalonil is e.g. 1:250 to 250:1, e.g. 1:100 to 100:1, e.g. 100:1 to 1:10, e.g. 100:1 to 1:1, e.g. 50:1 to 1:1.

In one embodiment the ratio of the compound of formula I to cyproconazole by weight in the composition may be 1:1 to 1:5. Examples of ratios falling within this range include 1:1.5, 1:2, 1:2.5, 1:3, 1:3.5, 1:4, 1:4.5. In another embodiment the ratio of formula I to cyproconazole may be 4000:1 or less, e.g. 1000:1 or less, e.g. 100:1 or less. For example the ratio of the compound of formula I to cyproconazole is e.g. 1:250 to 250:1, e.g. 1:100 to 100:1, e.g. 100:1 to 1:10, e.g. 100:1 to 1:1, e.g. 50:1 to 1:1.

In one embodiment the ratio of the compound of formula I to difenoconazole by weight in the composition may be 1:0.3 to 1:5. Examples of ratios falling within this range include 1:0.5, 1:0.7, 1:0.9, 1:1, 1:1.2, 1:1.4. In another embodiment the ratio of formula I to difenoconazole may be 4000:1 or less, e.g. 1000:1 or less, e.g. 100:1 or less. For example the ratio of the compound of formula I to difenoconazole is e.g. 1:250 to 250:1, e.g. 1:100 to 100:1, e.g. 100:1 to 1:10, e.g. 100:1 to 1:1, e.g. 50:1 to 1:1.

In one embodiment the ratio of the compound of formula I to mandipropamid by weight in the composition may be 1:1 to 1:15. Examples of ratios falling within this range include 1:2, 1:4, 1:6, 1:8, 1:10, 1:12, 1:14. In another embodiment the ratio of formula I to mandipropamid may be 4000:1 or less, e.g. 1000:1 or less, e.g. 100:1 or less. For example the ratio of the compound of formula I to mandipropamid is e.g. 1:250 to 250:1, e.g. 1:100 to 100:1, e.g. 100:1 to 1:10, e.g. 100:1 to 1:1, e.g. 50:1 to 1:1.

In one embodiment the ratio of the compound of formula I to mefenoxam by weight in the composition may be 1:0.3 to 1:8. Examples of ratios falling within this range include 1:1, 1:2, 1:3, 1:4, 1:5, 1:6, 1:7. In another embodiment the ratio of formula I to mefenoxam may be 4000:1 or less, e.g. 1000:1 or less, e.g. 100:1 or less. For example the ratio of the compound of formula I to mefenoxam is e.g. 1:250 to 250:1, e.g. 1:100 to 100:1, e.g. 100:1 to 1:10, e.g. 100:1 to 1:1, e.g. 50:1 to 1:1.

In one embodiment the ratio of the compound of formula I to the compound of formula IIIA by weight in the composition may be 1:0.3 to 1:8. Examples of ratios falling within this range include 1:1, 1:2, 1:3, 1:4, 1:5, 1:6, 1:7. In another embodiment the ratio of formula I to the compound of formula IIIA may be 4000:1 or less, e.g. 1000:1 or less, e.g. 100:1 or less. For example the ratio of the compound of formula I to the compound of formula IIIA is e.g. 1:250 to 250:1, e.g. 1:100 to 100:1, e.g. 100:1 to 1:10, e.g. 100:1 to 1:1, e.g. 50:1 to 1:1.

In one embodiment the ratio of the compound of formula I to the compound of formula IVA by weight in the composition may be 1:0.3 to 1:8. Examples of ratios falling within this range include 1:1, 1:2, 1:3, 1:4, 1:5, 1:6, 1:7. In another embodiment the ratio of formula I to the compound of formula IVA may be 4000:1 or less, e.g. 1000:1 or less, e.g. 100:1 or less. For example the ratio of the compound of formula I to the compound of formula IVA is e.g. 1:250 to 250:1, e.g. 1:100 to 100:1, e.g. 100:1 to 1:10, e.g. 100:1 to 1:1, e.g. 50:1 to 1:1.

The compounds of the invention may be made by a variety of methods as shown in Schemes 1 to 3.

carried out at a temperature of from 0° C. to 100° C., preferably from 15° C. to 30° C., in particular at ambient temperature Amines of formula (III) are either known in the literature or can be prepared using methods known to a person skilled in the art.

2) Acid halides of formula (II), wherein R is Cl, F or Br, may be made from carboxylic acids of formula (II), wherein R is OH, under standard conditions, as described for example in WO09080250.

3) Carboxylic acids of formula (II), wherein R is OH, may be formed from esters of formula (II), wherein R is $C_1$-$C_6$alkoxy as described for example in WO09080250.

4) Compounds of formula (I) can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis-(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethyl- Scheme 1

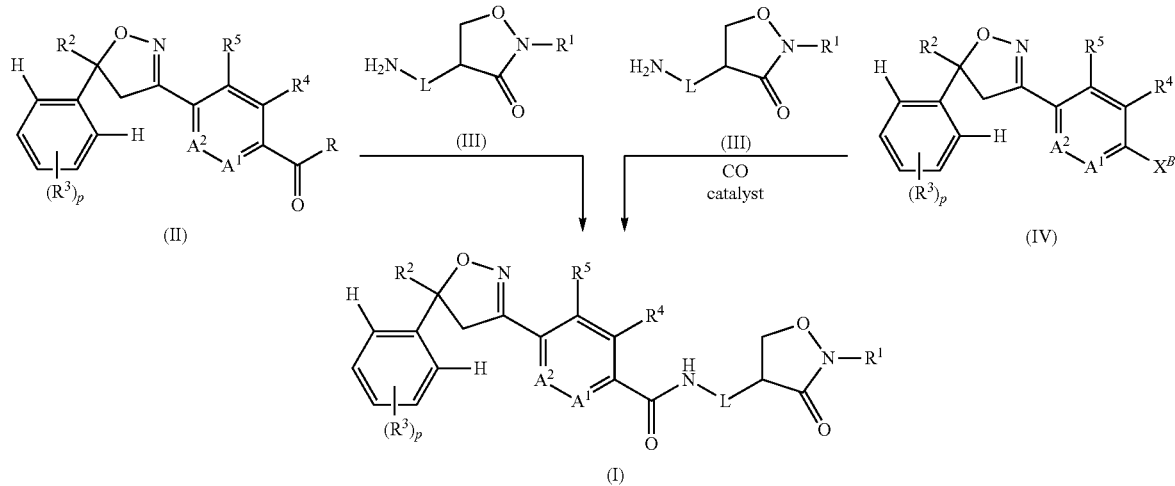

1) Compounds of formula (I), can be prepared by reacting a compound of formula (II) wherein R is OH, $C_1$-$C_6$alkoxy or Cl, F or Br, with an amine of formula (III) as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis (2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is formamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

5) Compounds of formula (IV) wherein $X^B$ is a leaving group, for example a halogen, such as bromo, can be made by a various of methods, for example as described in WO09080250.

Scheme 2

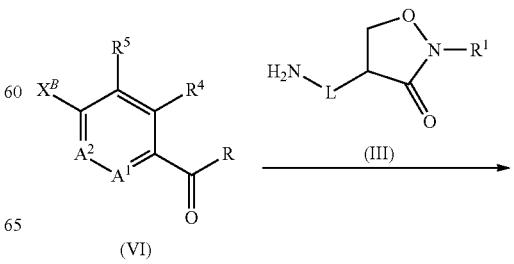

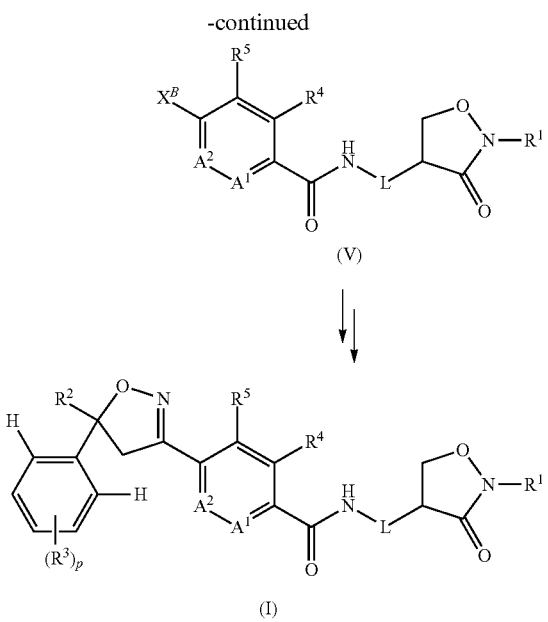

(V)

↓↓

(I)

6) Alternatively, compounds of formula (I), can be prepared by various methods from an intermediate of formula (V) as shown in Scheme 2 wherein $X^B$ is a leaving group, for example a halogen, such as bromo, or $X^B$ is cyano, formyl or acetyl according to similar methods to those described in WO09080250. An intermediate of formula (V) can be prepared for example from an intermediate of formula (VI) as described in the same reference.

Scheme 3

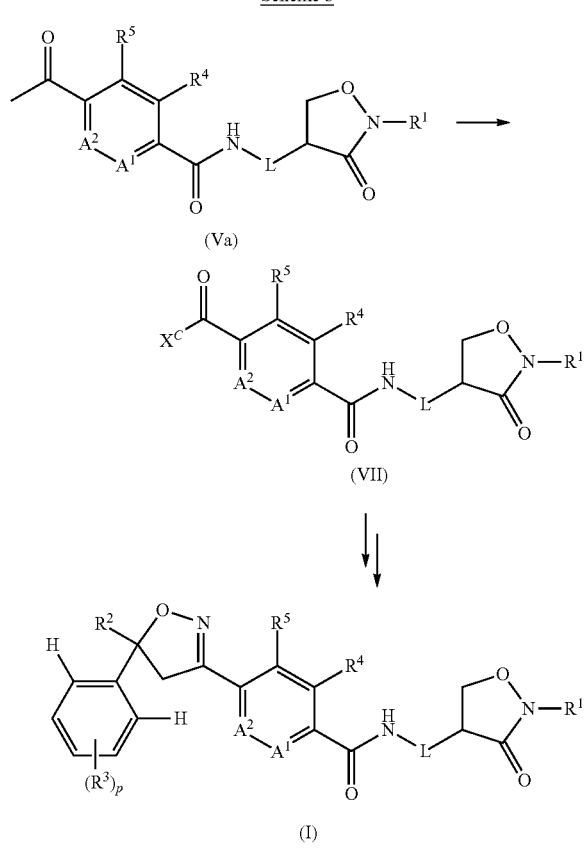

(Va)

↓

(VII)

↓↓

(I)

7) Alternatively, compounds of formula (I) can be prepared by various methods from an intermediate of formula (VII) as shown in Scheme 3 wherein $X^C$ is $X^C$-1 or $X^C$-2

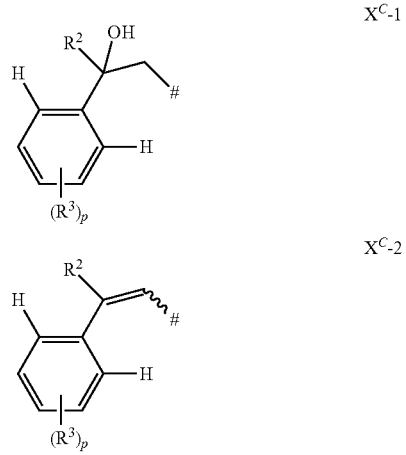

$X^C$-1

$X^C$-2 according to similar methods to those described in WO09080250.

8) Compounds of formula (VII) wherein $X^C$ is $X^C$ is $X^C$-1 or $X^C$-2 can be prepared from a compound of formula (Va) from a compound of formula (VII) wherein $X^C$ is $CH_2$-halogen using similar methods to those described in WO09080250.

9) Compounds of formula (VII) wherein $X^C$ is $CH_2$-halogen, such as bromo or chloro, can be prepared by reacting a methyl ketone of formula (Va) with a halogenating agent, such as bromine or chlorine, in a solvent, such as acetic acid, at a temperature of from 0° C. to 50° C., preferably from ambient temperature to 40° C.

Other methods for the preparation of compounds of formula I are described in PCT/EP2010/068605, which is incorporated herein by reference.

The present invention also relates to a method of controlling phytopathogenic diseases on useful plants or on propagation material thereof, which comprises applying to the useful plants, the locus thereof or propagation material thereof a combination of components A and B; a method of controlling insects, acarines, nematodes or molluscs which comprises applying to a pest, to a locus of a pest, or to a plant susceptible to attack by a pest a combination of components A and B; a seed comprising a pesticidal mixture of components A and B; a method comprising coating a seed with a mixture of components A and B.

Components A and B may be provided and/or used in amounts such that they are capable of synergistic pest control. For example, the present invention includes pesticidal mixtures comprising a component A and a component B in a synergistically effective amount; agricultural compositions comprising a mixture of component A and B in a synergistically effective amount; the use of a mixture of component A and B in a synergistically effective amount for combating animal pests; the use of a mixture of component A and B in a synergistically effective amount for combating phytopathogenic fungi; a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a mixture of component A and B in a synergistically effective amount; a method for protecting crops from attack or infestation by animal pests and/or phythopathogenic fungi, which comprises contacting a crop with a mixture of component A and B in a synergistically effective amount; a method for the protection of seeds from soil insects and of the seedlings' roots and shoots from soil and foliar insects and/or phythopathogenic fungi comprising contacting the seeds before sowing and/or after pre-germination with a mixture of component A and B in a synergistically effective amount; seeds comprising, e.g. coated with, a mixture of component A and B in a synergistically effective amount; a method comprising coating a seed with a mixture of component A and B in a synergistically effective amount; a method of controlling phytopathogenic, e.g. fungal, diseases on useful plants or on propagation material thereof, which comprises applying to the useful plants, the locus thereof or propagation material thereof a combination of components A and B in a synergistically effective amount. In such applications the mixtures of A and B will normally be applied in a fungicidally effective amount. The invention also provides a method of controlling insects, acarines, nematodes or molluscs which comprises applying to a pest, to a locus of a pest, or to a plant susceptible to attack by a pest a combination of components A and B in a synergistically effective amount. In such applications mixtures of A and B will normally be applied in an insecticidally, acaricidally, nematicidally or molluscicidally effective amount. In application components A and B may be applied simultaneously or separately.

The active ingredient combinations are effective against harmful microorganisms, such as microorganisms, that cause phytopathogenic diseases, in particular against phytopathogenic fungi and bacteria. The active ingredient combinations are effective especially against phytopathogenic fungi belonging to the following classes: Ascomycetes (e.g. *Venturia, Podosphaera, Erysiphe, Monilinia, Mycosphaerella, Uncinula*); Basidiomycetes (e.g. the genus *Hemileia, Rhizoctonia, Phakopsora, Puccinia, Ustilago, Tilletia*); Fungi imperfecti (also known as Deuteromycetes; e.g. *Botrytis, Helminthosporium, Rhynchosporium, Fusarium, Septoria, Cercospora, Alternaria, Pyricularia* and *Pseudocercosporella*); Oomycetes (e.g. *Phytophthora, Peronospora, Pseudoperonospora, Albugo, Bremia, Pythium, Pseudosclerospora, Plasmopara*).

The mixtures of the invention, in particular those in the tables above, may be used for soil applications, including as a seed application, to target at least the following: early foliar diseases such as *Phakopsora Pachyrihizi, Septoria* (e.g. cereals) and other leafspot diseases, cereal rusts and powdery mildew; seed borne disease such as Smuts (e.g. *Ustilago, Spacelotheca*) on e.g. ceareals and corn, snow mould (e.g. *Micodochium*) on e.g. cereals, *Fusarium* on e.g. cereals, corn, potato, rice, cotton, vegetables, stripe disease (e.g. *Pyrenophora*) on e.g. barley, *Pyricularia* and *Helminthosporium* e.g. on rice, potatoes, *Phoma* and *Ascochyta* e.g. on pulse crops, oil seed rape and soybean, bunts (e.g. *Tilletia*) e.g. on wheat, *Aspergillus* and *Penicillium* e.g. on corn, soybean, *Dipoldia* and *Colletotrichum* e.g. on corn, *Cochliobolus* and *septoria* e.g. on cereals; soil borne diseases such as *Rhizoctonia* (applicable to many crops), *Fusarium* e.g. on cereals, corn, soybean and cotton, take-all e.g. on wheat, eyespot on e.g. wheat, *Thielaviopsis* on e.g. cotton; oomycetes such as *Pythium* spp., downy mildews such as *Plasmopora, Aphanomycetes* (e.g. on sugar beet); sucking pests such as aphids, *thrips*, brown plant hopper (e.g. on rice), sting bugs, white flies (e.g. on cotton and vegetables), mites; on soil pests such as corn root worm, wireworms, white grubs, *zabrus*, termites (e.g. on sugar cane, soy, pasture), maggots, cabbage root fly, red legged earth mite; on lepidoptera, such as *spodoptera*, cutworms, elasmoplpus, *plutella* (e.g. *brassica*), stem borers, leaf miners, flea beetle, *Sternechus*; on nematicides, such as *Heterodera glycines* (e.g. on soybean), *Pratylenchus brachyurus* (e.g. on corn), *P. zeae* (e.g. on corn), *P. penetrans* (e.g. on corn), *Meloidogyne incognita* (e.g. on vegetables), *Heterodera schachtii* (e.g. on sugar beet), *Rotylenchus reniformis* (e.g. on cotton), *Heterodera avenae* (e.g. on cereals), *Pratylenchus neglectus* (e.g. on cereals), *thornei* (e.g. on cereals).

The mixtures of the present invention can be used to control infestations of insect pests such as Lepidoptera, Diptera, Hemiptera, Thysanoptera, Orthoptera, Dictyoptera, Coleoptera, Siphonaptera, Hymenoptera and *Isoptera* and also other invertebrate pests, for example, acarine, nematode and mollusc pests. Insects, acarines, nematodes and molluscs are hereinafter collectively referred to as animal pests. The animal pests which may be controlled by the use of the invention compounds include those animal pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The mixtures of the invention are particularly effective against insects, acarines and/or nematodes.

According to the invention "useful plants" typically comprise the following species of plants: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Compounds of formula I and mixtures of the invention may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in superadditive "synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected. Such synergistic effects with the transgenic crop can be obtained when applied for control of soil pests (e.g. seed care or in-furrow treatments) as well as after emergence, in particular for corn and soybean.

Use of the compounds of formula I and the mixtures of the invention can also be applied as a seed care treatment with transgenic crops in resistance management strategies for the trait (particularly inseciticidal traits), e.g. including in corn and soybean.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes).

Compounds of formula I and mixtures of the invention may be used on transgenic plants that are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030,295) or Cry1A.105; or vegetative insecticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (P1) (corn producing Cry1Ab), Agrisure®RW (P2) (corn producing mCry3A), Agrisure® Viptera (P3) (corn hybrids producing Vip3Aa); Agrisure300GT (P4) (corn hybrids producing Cry1Ab and mCry3A); YieldGard® (P5) (corn hybrids producing the Cry1Ab protein), YieldGard® Plus (P6) (corn hybrids producing Cry1Ab and Cry3Bb1), Genuity® SmartStax® (P7) (corn hybrids with Cry1A.105, Cry2Ab2, Cry1F, Cry34/35, Cry3Bb); Herculex® I (P8) (corn hybrids producing Cry1Fa) and Herculex®RW (P9) (corn hybrids producing Cry34Ab1, Cry35Ab1 and the enzyme Phosphinothricin-N-Acetyltransferase [PAT]); NuCOTN®33B (P10) (cotton cultivars producing Cry1Ac), Bollgard®I (P11) (cotton cultivars producing Cry1Ac), Bollgard®II (P12) (cotton cultivars producing Cry1Ac and Cry2Ab2) and VIPCOT® (P13) (cotton cultivars producing a Vip3Aa). Soybean Cyst Nematode resistance soybean (SCN®—Syngenta (P14)) and soybean with Aphid resistant trait (AMT® (P15)) are also of interest.

Further examples of such transgenic crops are:

1. Bt11 Maize from Syngenta Seeds SAS, Chemin de l'Hobit 27, F-31 790 St. Sauveur, France, registration number C/FR/96/05/10 (P16). Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10 (P17). Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10 (P18). Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9 (P19). MON 863 expresses a CryIIIB (b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02. (P20)

6. 1507 Maize from Pioneer Overseas Corporation, Avenue Tedesco, 7 B-1160 Brussels, Belgium, registration number C/NL/00/10. (P21) Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03 (P22). Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Further examples of transgenic plants, and of very high interest, are those carrying traits conferring resistance to 2.4D (e.g. Enlist®) (e.g. WO 2011066384) (P23), glyphosate (e.g. Roundup Ready®, Roundup Ready 2 Yield® (P25)), sulfonylurea (e.g. STS®), glufosinate (e.g. Liberty Link®, Ignite®), Dicamba (Monsanto), HPPD tolerance (e.g. isoxaflutole herbicide, mesotrione herbicide—US7312379) (Bayer CropScience, Syngenta). Double or triple stacks of any of the traits described here are also of interest, including glyphosate and sulfonyl-urea tolerance ((e.g. Optimum GAT®), plants stacked with STS® and Roundup Ready® or plants stacked with STS® and Roundup Ready 2 Yield®, dicamba and glyphosate tolerance (Monsanto). Of particular interest are soybean plants carrying trains conferring resistance to 2.4D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonyl-urea tolerance (e.g. Optimum GAT®, plants stacked with STS® and Roundup Ready® or Roundup Ready 2 Yield®), dicamba and glyphosate tolerance (Monsanto).

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds. Fungicides that are of particular interest for treating seeds include Fludioxonil, Thiabendazole, Sedaxane, Mefenoxam and Metalaxyl. Accordingly, in one embodiment component B is selected from Fludioxonil, Thiabendazole, Sedaxane, Mefenoxam and Metalaxyl.

Further combination of interest, particularly for seed care, include mixtures of compounds of formula I with the mixtures described in: WO2006/015865 and WO2007/090623, in particular those described in the Examples. Of particular interest are the following combinations: a compound of formula I+sedaxane+mefenoxam+difenoconazole, a compound of formula I+fludioxonil+sedaxane+difenoconazole, a compound of formula I+fludioxonil+sedaxane+difenoconazole+thiamethoxam, a compound of formula I+fludioxonil+mefenoxam+sedaxane+thiabendazole, a compound of formula I+fludioxonil+difenoconazole+sedaxane+a compound of formula I+fludioxonil+sedaxane+mefenoxam. Example or ratios are below.

Methods for applying or treating active ingredients on to plant propagation material, especially seeds, are known in the art, and include dressing, coating, pelleting and soaking application methods of the propagation material. Conventional treating techniques and machines can be used, such as fluidized beds, roller mills, rotostatic seed treaters, drum coaters, and spouted beds.

Methods of applying to the soil can be via any suitable method, which ensures that the combination penetrates the soil, for example, nursery tray application, in furrow application, soil drenching, soil injection, drip irrigation, application through sprinklers or central pivot, incorporation into soil (broad cast or in band) are such methods. Alternatively or in addition one or more materials may be applied on a suitable substrate, for example a seed which is not intended for germination, and "sowing" the treated substrate with the plant propagation material.

Even distribution of ingredients and good adherence is particularly desired for seed treatment. Treatment could vary from a thin film or dressing of the formulation, for example, a mixture of active ingredients, on a plant propagation material, such as a seed, where the original size and/or shape are recognizable to an intermediary state to a thicker film such as pelleting with many layers of different materials (such as carriers, for example, clays; different formulations, such as of other active ingredients; polymers; and colourants) where the original shape and/or size of the seed is no longer recognisable.

Application onto plant propagation material can include controlled release coatings, wherein the ingredients of the combinations are incorporated into materials that release the ingredients over time. Examples of controlled release technologies are generally known in the art and include polymer films and waxes, wherein the ingredients may be incorporated into the controlled release material or applied between layers of materials, or both.

A further aspect of the instant invention is a method of protecting natural substances of plant and/or animal origin, which have been taken from the natural life cycle, and/or their processed forms against attack of fungi and/or animal pests, which comprises applying to said natural substances of plant and/or animal origin or their processed forms a combination of components A and B in a synergistically effective amount. Such applications include use of the mixtures of the invention as a treatment, for example a fumigant, for stored grain to protect against attack of invertabrate pests and or fungi. It may be noted that compounds of formula I may be used alone as a treatment for stored grain to protect against attack of invertabrate pests.

According to the instant invention, the term "natural substances of plant origin, which have been taken from the natural life cycle" denotes plants or parts thereof which have been harvested from the natural life cycle and which are in the freshly harvested form. Examples of such natural substances of plant origin are stalks, leafs, tubers, seeds, fruits or grains. According to the instant invention, the term "processed form of a natural substance of plant origin" is understood to denote a form of a natural substance of plant origin that is the result of a modification process. Such modification processes can be used to transform the natural substance of plant origin in a more storable form of such a substance (a storage good). Examples of such modification processes are pre-drying, moistening, crushing, comminuting, grounding, compressing or roasting. Also falling under the definition of a processed form of a natural substance of plant origin is timber, whether in the form of crude timber, such as construction timber, electricity pylons and barriers, or in the form of finished articles, such as furniture or objects made from wood.

According to the instant invention, the term "natural substances of animal origin, which have been taken from the natural life cycle and/or their processed forms" is understood to denote material of animal origin such as skin, hides, leather, furs, hairs and the like. The combinations according the present invention can prevent disadvantageous effects such as decay, discoloration or mould.

A preferred embodiment is a method of protecting natural substances of plant origin, which have been taken from the natural life cycle, and/or their processed forms against attack of fungi and/or animal pests, which comprises applying to said natural substances of plant and/or animal origin or their processed forms a combination of components A and B in a synergistically effective amount.

A further preferred embodiment is a method of protecting fruits, preferably pomes, stone fruits, soft fruits and citrus fruits, which have been taken from the natural life cycle, and/or their processed forms, which comprises applying to said fruits and/or their processed forms a combination of components A and B in a synergistically effective amount.

The combinations of the present invention may also be used in the field of protecting industrial material against attack of fungi. According to the instant invention, the term "industrial material" denotes non-living materials which have been prepared for use in industry. For example, industrial materials which are intended to be protected against attack of fungi can be glues, sizes, paper, board, textiles, carpets, leather, wood, constructions, paints, plastic articles, cooling lubricants, aquaeous hydraulic fluids and other materials which can be infested with, or decomposed by, microorganisms. Cooling and heating systems, ventilation and air conditioning systems and parts of production plants, for example cooling-water circuits, which may be impaired by multiplication of microorganisms may also be mentioned from amongst the materials to be protected. The combinations according the present invention can prevent disadvantageous effects such as decay, discoloration or mold.

The combinations of the present invention may also be used in the field of protecting technical material against attack of fungi. According to the instant invention, the term "technical material" includes paper; carpets; constructions; cooling and heating systems; ventilation and air conditioning systems and the like. The combinations according the present invention can prevent disadvantageous effects such as decay, discoloration or mold.

The combinations according to the present invention are particularly effective against powdery mildews; rusts; leafspot species; early blights and molds; especially against *Septoria, Puccinia, Erysiphe, Pyrenophora* and *Tapesia* in cereals; *Phakopsora* in soybeans; *Hemileia* in coffee; *Phragmidium* in roses; *Alternaria* in potatoes, tomatoes and cucurbits; *Sclerotinia* in turf, vegetables, sunflower and oil seed rape; black rot, red fire, powdery mildew, grey mold and dead arm disease in vine; *Botrytis cinerea* in fruits; *Monilinia* spp. in fruits and *Penicillium* spp. in fruits.

The combinations according to the present invention are furthermore particularly effective against seedborne and soilborne diseases, such as *Alternaria* spp., *Ascochyta* spp., *Botrytis cinerea, Cercospora* spp., *Claviceps purpurea, Cochliobolus sativus, Colletotrichum* spp., *Epicoccum* spp., *Fusarium graminearum, Fusarium moniliforme, Fusarium oxysporum, Fusarium proliferatum, Fusarium solani, Fusarium subglutinans, Gäumannomyces graminis, Helminthosporium* spp., *Microdochium nivale, Phoma* spp., *Pyrenophora graminea, Pyricularia oryzae, Rhizoctonia solani, Rhizoctonia cerealis, Sclerotinia* spp., *Septoria* spp., *Sphacelotheca reilliana, Tilletia* spp., *Typhula incarnata, Urocystis occulta, Ustilago* spp. or *Verticillium* spp.; in particular against pathogens of cereals, such as wheat, barley, rye or oats; maize; rice; cotton; soybean; turf; sugarbeet; oil seed rape; potatoes; pulse crops, such as peas, lentils or chickpea; and sunflower.

The combinations according to the present invention are furthermore particularly effective against post harvest diseases such as *Botrytis cinerea, Colletotrichum musae, Curvularia lunata, Fusarium semitecum, Geotrichum candidum, Monilinia fructicola, Monilinia fructigena, Monilinia laxa, Mucor piriformis, Penicilium italicum, Penicilium solitum, Penicillium digitatum* or *Penicillium expansum* in particular against pathogens of fruits, such as pomefruits, for example apples and pears, stone fruits, for example peaches and plums, citrus, melons, papaya, kiwi, mango, berries, for example strawberries, avocados, pomegranates and bananas, and nuts.

The combinations according to the invention are particularly useful for controlling the following plant diseases:

*Alternaria* species in fruit and vegetables,
*Ascochyta* species in pulse crops,
*Botrytis cinerea* in strawberries, tomatoes, sunflower, pulse crops, vegetables and grapes,
*Cercospora arachidicola* in peanuts,
*Cochliobolus sativus* in cereals,
*Colletotrichum* species in pulse crops,
*Erysiphe* species in cereals,
*Erysiphe cichoracearum* and *Sphaerotheca fuliginea* in cucurbits,
*Fusarium* species in cereals and maize,
*Gäumannomyces graminis* in cereals and lawns,

*Helminthosporium* species in maize, rice and potatoes,
*Hemileia vastatrix* on coffee,
*Microdochium* species in wheat and rye,
*Phakopsora* species in soybean,
*Puccinia* species in cereals, broadleaf crops and perrenial plants,
*Pseudocercosporella* species in cereals,
*Phragmidium mucronatum* in roses,
*Podosphaera* species in fruits,
*Pyrenophora* species in barley,
*Pyricularia oryzae* in rice,
*Ramularia collo-cygni* in barley,
*Rhizoctonia* species in cotton, soybean, cereals, maize, potatoes, rice and lawns,
*Rhynchosporium secalis* in barley and rye,
*Sclerotinia* species in lawns, lettuce, vegetables and oil seed rape,
*Septoria* species in cereals, soybean and vegetables,
*Sphacelotheca reilliana* in maize,
*Tilletia* species in cereals,
*Uncinula necator, Guignardia bidwellii* and *Phomopsis viticola* in vines,
*Urocystis occulta* in rye,
*Ustilago* species in cereals and maize,
*Venturia* species in fruits,
*Monilinia* species on fruits,
*Penicillium* species on citrus and apples.

The compounds of formula (I) and mixtures of the invention can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the compounds of the invention include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The compounds of the invention may be used for example on turf, ornamentals, such as flowers, shrubs, broad-leaved trees or evergreens, for example conifers, as well as for tree injection, pest management and the like. Compositions comprising the compound of formula I may be used on ornamental garden plants (e.g. flowers, shrubs, broad-leaved trees or evergreens), e.g. to control aphids, whitefly, scales, meelybug, beetles and caterpillars. Compositions comprising the compound of formula I may be used on garden plants (e.g. flowers, shrubs, broad-leaved trees or evergreens), on indoor plants (e.g. flowers and shrubs) and on indoor pest e.g. to control aphids, whitefly, scales, meelybug, beetles and caterpillars.

Furthermore, the compounds of formula (I) and mixtures of the invention may be effective against harmful insects, without substantially imposing any harmful side effects to cultivated plants. Application of the compounds of the invention may increase the harvest yields, and may improve the quality of the harvested material. The compounds of the invention may have favourable properties with respect to amount applied, residue formulation, selectivity, toxicity, production methodology, high activity, wide spectrum of control, safety, control of resistant organisms, e.g. pests that are resistant to organic phosphorus agents and/or carbamate agents.

Examples of pest species which may be controlled by compounds of formula (I) and mixtures of the invention include: coleopterans, for example, *Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus, Lyctus bruneus, Aulacophora femoralis;* lepidopterans, for example, *Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotisfucosa, Galleria mellonella, Plutella maculipennis, Heliothis virescens, Phyllocnistis citrella;* hemipterans, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara* spp., *Trialeurodes vaporariorm, Psylla* spp.; thysanopterans, for example, *Thrips palmi, Franklinella occidental;* orthopterans, for example, *Blatella germanica, Periplaneta americana, Gryllotalpa Africana, Locusta migratoria migratoriodes;* isopterans, for example, *Reticulitermes speratus, Coptotermes formosanus;* dipterans, for example, *Musca domestica, Aedes aegypti, Hylemia platura, Culex pipiens, Anopheles sinensis, Culex tritaeniorhynchus, Liriomyza trifolii;* acari, for example, *Tetranychus cinnabarinus, Tetranychus urticae, Panonychus citri, Aculops pelekassi, Tarsonemus* spp.; nematodes, for example, *Meloidogyne incognita, Bursaphelenchus lignicolus Mamiya et Kiyohara, Aphelenchoides besseyi, Heterodera glycines, Pratylenchus* spp.

Examples of further pest species which may be controlled by compounds of formula (I) and mixtures of the invention include: from the order of the *Anoplura (Phthiraptera)*, for example, *Damalinia* spp., *Haematopinus* spp., *Linognathus* spp., *Pediculus* spp., *Trichodectes* spp.; from the class of the *Arachnida*, for example, *Acarus siro, Aceria sheldoni, Aculops* spp., *Aculus* spp., *Amblyomma* spp., *Argas* spp., *Boophilus* spp., *Brevipalpus* spp., *Biyobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;* from the class of the *Bivalva*, for example, *Dreissena* spp.; from the order of the *Chilopoda*, for example, *Geophilus* spp., *Scutigera* spp.; from the order of the *Coleoptera*, for example, *Acanthoscehdes obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus* xanthographus, Niptus hololeucus, Oryctes rhinoceros, Oryzaephilus surinamensis, Otiorrhynchus sulcatus, Oxycetonia jucunda, Phaedon cochleariae, Phyllophaga spp., Popillia japonica, Premnotrypes spp., Psylliodes chrysocephala, Ptinus spp., Rhizobius ventralis, Rhizopertha dominica, Sitophilus spp., Sphenophorus spp., Sternechus spp., Symphyletes spp., Tenebrio molitor, Tribolium spp., Trogoderma spp., Tychius spp., Xylotrechus spp., Zabrus spp.; from the order of the Collembola, for example, Onychiurus armatus; from the order of the Dermaptera, for example, Forficula auricularia; from the order of the Diplopoda, for example, Blaniulus guttulatus; from the order of the Diptera, for example, Aedes spp., Anopheles spp., Bibio hortulanus, Calliphora erythrocephala, Ceratitis capitata, Chrysomyia spp., Cochliomyia spp., Cordylobia anthropophaga, Culex spp., Cuterebra spp., Dacus oleae, Dermatobia hominis, Drosophila spp., Fannia spp., Gastrophilus spp., Hylemyia spp., Hyppobosca spp., Hypoderma spp., Liriomyza spp., Lucilia spp., Musca spp., Nezara spp., Oestrus spp., Oscinella frit, Pegomyia hyoscyami, Phorbia spp., Stomoxys spp., Tabanus spp., Tannia spp., Tipula paludosa, Wohlfahrtia spp.; from the class of the Gastropoda, for example, Anon spp., Biomphalaria spp., Bulinus spp., Deroceras spp., Galba spp., Lymnaea spp., Oncomelania spp., Succinea spp.; from the class of the helminths, for example, Ancylostoma duodenale, Ancylostoma ceylanicum, Acylostoma braziliensis, Ancylostoma spp., Ascaris lubricoides, Ascaris spp., Brugia malayi, Brugia timori, Bunostomum spp., Chabertia spp., Clonorchis spp., Cooperia spp., Dicrocoelium spp, Dictyocaulus filaria, Diphyllobothrium latum, Dracunculus medinensis, Echinococcus granulosus, Echinococcus multilocularis, Enterobius vermicularis, Faciola spp., Haemonchus spp., Heterakis spp., Hymenolepis nana, Hyostrongulus spp., Loa Loa, Nematodirus spp., Oesophagostomum spp., Opisthorchis spp., Onchocerca volvulus, Ostertagia spp., Paragonimus spp., Schistosomen spp., Strongyloides fuelleborni, Strongyloides stercoralis, Stronyloides spp., Taenia saginata, Taenia solium, Trichinella spiralis, Trichinella nativa, Trichinella britovi, Trichinella nelsoni, Trichinella pseudopsiralis, Trichostrongulus spp., Trichuris trichuria, Wuchereria bancrofti; ft may be furthermore possible to control protozoa, such as Eimeria; from the order of the Heteroptera, for example, Anasa tristis, Antestiopsis spp., Blissus spp., Calocoris spp., Campylomma livida, Cavelerius spp., Cimex spp., Creontiades dilutus, Dasynus piperis, Dichelops furcatus, Diconocoris hewetti, Dysdercus spp., Euschistus spp., Eurygaster spp., Heliopeltis spp., Horcias nobilellus, Leptocorisa spp., Leptoglossus phyllopus, Lygus spp., Macropes excavatus, Miridae, Nezara spp., Oebalus spp., Pentomidae, Piesma quadrata, Piezodorus spp., Psallus seriatus, Pseudacysta persea, Rhodnius spp., Sahlbergella singularis, Scotinophora spp., Stephanitis nashi, Tibraca spp., Triatoma spp.; from the order of the Homoptera, for example, Acyrthosipon spp., Aeneolamia spp., Agonoscena spp., Aleurodes spp., Aleurolobus barodensis, Aleurothrixus spp., Amrasca spp., Anuraphis cardui, Aonidiella spp., Aphanostigma pini, Aphis spp., Arboridia apicalis, Aspidiella spp., Aspidiotus spp., Atanus spp., Aulacorthum solani, Bemisia spp., Brachycaudus helichrysii, Brachycolus spp., Brevicoryne brassicae, Calligypona marginata, Carneocephala fulgida, Ceratovacuna lanigera, Cercopidae, Ceroplastes spp., Chaetosiphon fragaefolii, Chionaspis tegalensis, Chlorita onukii, Chromaphis juglandicola, Chrysomphalus ficus, Cicadulina mbila, Coccomytilus halli, Coccus spp., Cryptomyzus ribis, Dalbulus spp., Dialeurodes spp., Diaphorina spp., Diaspis spp., Doralis spp., Drosicha spp., Dysaphis spp., Dysmicoccus spp., Empoasca spp., Eriosoma spp., Erythroneura spp., Euscelis bilobatus, Geococcus coffeae, Homalodisca coagulata, Hyalopterus arundinis, Icerya spp., Idiocerus spp., Idioscopus spp., Laodelphax striatellus, Lecanium spp., Lepidosaphes spp., Lipaphis erysimi, Macrosiphum spp., Mahanarva fimbriolata, Melanaphis sacchari, Metcalfiella spp., Metopolophium dirhodum, Monellia costalis, Monelliopsis pecanis, Myzus spp., Nasonovia ribisnigri, Nephotettix spp., Nilaparvata lugens, Oncometopia spp., Orthezia praelonga, Parabemisia myricae, Paratrioza spp., Parlatoria spp., Pemphigus spp., Peregrinus maidis, Phenacoccus spp., Phloeomyzus passerinii, Phorodon humuli, Phylloxera spp., Pinnaspis aspidistrae, Planococcus spp., Protopulvinaria pyriformis, Pseudaulacaspis pentagona, Pseudococcus spp., Psylla spp., Pteromalus spp., Pyrilla spp., Quadraspidiotus spp., Quesada gigas, Rastrococcus spp., Rhopalosiphum spp., Saissetia spp., Scaphoides titanus, Schizaphis graminum, Selenaspidus articulatus, Sogata spp., Sogatella furcifera, Sogatodes spp., Stictocephala festina, Tenalaphara malayensis, Tinocallis caryaefoliae, Tomaspis spp., Toxoptera spp., Trialeurodes vaporariorum, Trioza spp., Typhlocyba spp., Unaspis spp., Viteus vitifolii; from the order of the Hymenoptera, for example, Diprion spp., Hoplocampa spp., Lasius spp., Mono-morium pharaonic, Vespa spp.; from the order of the Isopoda, for example, Armadillidium vulgare, Oniscus asellus, Porcellio scaber; from the order of the Isoptera, for example, Reticulitermes spp., Odontotermes spp.; from the order of the Lepidoptera, for example, Acronicta major, Aedia leucomelas, Agrotis spp., Alabama argillacea, Anticarsia spp., Barathra brassicae, Bucculatrix thurberiella, Bupalus piniarius, Cacoecia podana, Capua reticulana, Carpocapsa pomonella, Chematobia brumata, Chilo spp., Choristoneura fumiferana, Clysia ambiguella, Cnaphalocerus spp., Earias insulana, Ephestia kuehniella, Euproctis chrysorrhoea, Euxoa spp., Feltia spp., Galleria mellonella, Helicoverpa spp., Heliothis spp., Hofmannophila pseudospretella, Homona magnanima, Hyponomeuta padella, Laphygma spp., Lithocolletis blancardella, Lithophane antennata, Loxagrotis albicosta, Lymantria spp., Malacosoma neustria, Mamestra brassicae, Mocis repanda, Mythimna separata, Oria spp., Oulema oryzae, Panolis flammea, Pectinophora gossypiella, Phyllocnistis citrella, Pieris spp., Plutella xylostella, Prodenia spp., Pseudaletia spp., Pseudoplusia includens, Pyrausta nubilalis, Spodoptera spp., Thermesia gemmatalis, Tinea pellionella, Tineola bisselliella, Tortrix viridana, Trichoplusia spp.; from the order of the Orthoptera, for example, Acheta domesticus, Blatta orientalis, Blattella germanica, Gryllotalpa spp., Leucophaea maderae, Locusta spp., Melanoplus spp., Periplaneta americana, Schistocerca gregaria; from the order of the Siphonaptera, for example, Ceratophyllus spp., Xenopsylla cheopis. From the order of the Symphyla, for example, Scutigerella immaculata; from the order of the Thysanoptera, for example, Baliothrips biformis, Enneothrips flavens, Frankliniella spp., Heliothrips spp., Hercinothrips femoralis, Kakothrips spp., Rhipiphorothrips cruentatus, Scirtothrips spp., Taeniothrips cardamoni, Thrips spp.; from the order of the Thysanura, for example, Lepisma saccharina. The phytoparasitic nematodes include, for example, Anguina spp., Aphelenchoides spp., Belonoaimus spp., Bursaphelenchus spp., Ditylenchus dipsaci, Globodera spp., Heliocotylenchus spp., Heterodera spp., Longidorus spp., Meloidogyne spp., Pratylenchus spp., Radopholus similis, Rotylenchus spp., Trichodorus spp., Tylenchorhynchus spp., Tylenchulus spp., Tylenchulus semipenetrans, Xiphinema spp.

The combinations according to the present invention are furthermore particularly effective against the following pests: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The compound of formula I and mixtures of the invention may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables, cucurbits and pulses (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The mixtures of the invention may be used for pest control on various plants, including soybean, corn, sugarcane, alfalfa, brassicas, oilseed rape (e.g. canola), potatoes (including sweet potatoes), cotton, rice, coffee, citrus, almonds, fruiting vegetables, cucurbits and pulses (e.g. tomatoes, pepper, chili, eggplant, cucumber, squash etc.), tea, bulb vegetables (e.g. onion, leek etc.), grapes, pome fruit (e.g. apples, pears etc.), stone fruit (e.g. pears, plums etc.), and cereals.

The mixtures of the invention may be used on soybean to control, for example, *Elasmopalpus lignosellus, Diloboderus abderus, Diabrotica speciosa, Trialeurodes* spp., *Bemisia* spp., aphids, *Sternechus subsignatus*, Formicidae, *Agrotis ypsilon, Julus* spp., *Murgantia* spp., *Halyomorpha* spp., *Thyanta* spp., *Megascelis* ssp., *Procornitermes* ssp., Gryllotalpidae, *Nezara viridula, Piezodorus* spp., *Acrosternum* spp., *Neomegalotomus* spp., *Cerotoma trifurcata, Popillia japonica, Edessa* spp., *Liogenys fuscus, Euschistus heros*, stalk borer, *Scaptocoris castanea, phyllophaga* spp., *Migdolus* spp., *Pseudoplusia includens, Anticarsia gemmatalis, Epinotia* spp., *Rachiplusia* spp., *Spodoptera* spp., *Bemisia tabaci, Tetranychus* spp., *Agriotes* spp., *Euschistus* spp. The mixtures of the invention are preferably used on soybean to control *Diloboderus abderus, Diabrotica speciosa, Trialeurodes* spp., *Bemisia* spp., *Nezara viridula, Piezodorus* spp., *Acrosternum* spp., *Cerotoma trifurcata, Popillia japonica, Euschistus heros, Scaptocoris castanea, phyllophaga* spp., *Migdolus* spp., *Agriotes* spp., *Euschistus* spp.

The mixtures of the invention may be used on corn to control, for example, *Euschistus heros, Euschistus* spp., *Dichelops furcatus, Diloboderus abderus, Thyanta* spp., *Elasmopalpus lignosellus, Halyomorpha* spp., *Spodoptera frugiperda, Nezara viridula, Cerotoma trifurcata, Popillia japonica, Agrotis ypsilon, Diabrotica speciosa*, aphids, Heteroptera, *Procornitermes* spp., *Scaptocoris castanea*, Formicidae, *Julus* ssp., *Dalbulus maidis, Diabrotica virgifera, Diabrotica* spp., *Mocis latipes, Bemisia tabaci*, heliothis spp., *Tetranychus* spp., thrips spp., *phyllophaga* spp., *Migdolus* spp., *scaptocoris* spp., *Liogenys fuscus, Spodoptera* spp., *Ostrinia* spp., *Sesamia* spp., wireworms, *Agriotes* spp., *Halotydeus destructor*. The mixtures of the invention are preferably used on corn to control *Euschistus heros, Euschistus* spp., *Dichelops furcatus, Diloboderus abderus, Nezara viridula, Cerotoma trifurcata, Popillia japonica, Diabrotica speciosa, Diabrotica virgifera, Diabrotica* spp., *Tetranychus* spp., *Thrips* spp., *Phyllophaga* spp., *Migdolus* spp., *Scaptocoris* spp., *Agriotes* spp.

The mixtures of the invention may be used on sugar cane to control, for example, *Sphenophorus* spp., termites, *Migdolus* spp., *Diloboderus* spp., *Telchin licus, Diatrea saccharalis, Mahanarva* spp., Mealybugs.

The mixtures of the invention may be used on alfalfa to control, for example, *Hypera brunneipennis, Hypera postica, Colias eurytheme, Collops* spp., *Empoasca solana, Epitrix* spp., *Geocoris* spp., *Lygus hesperus, Lygus lineolaris, Spissistilus* spp., *Spodoptera* spp., Aphids, *Trichoplusia ni*. The mixtures of the invention are preferably used on alfalfa to control *Hypera brunneipennis, Hypera postica, Empoasca solana, Epitrix* spp., *Lygus hesperus, Lygus lineolaris, Trichoplusia ni*.

The mixtures of the invention may be used on brassicas to control, for example, *Plutella xylostella, Pieris* spp., *Mamestra* spp., *Plusia* spp., *Trichoplusia ni, Phyllotreta* spp., *Spodoptera* spp., *Empoasca* spp., thrips spp., *Delia* spp., *Murgantia* spp., *Trialeurodes* spp., *Bemisia* spp., *Microtheca* spp., Aphids. The mixtures of the invention are preferably used on brassicas to control *Plutella xylostella, Pieris* spp., *Plusia* spp., *Trichoplusia ni, Phyllotreta* spp., *Thrips* spp.

The mixtures of the invention may be used on oil seed rape, e.g. canola, to control, for example, *Meligethes* spp., *Ceutorhynchus napi, Halotydeus destructor, Psylloides* spp.

The mixtures of the invention may be used on potatoes, including sweet potatoes, to control, for example, *Empoasca* spp., *Leptinotarsa* spp., *Diabrotica speciosa, Phthorimaea* spp., *Paratrioza* spp., *Maladera matrida, Agriotes* spp., Aphids, wireworms. The mixtures of the invention are preferably used on potatoes, including sweet potatoes, to control *Empoasca* spp., *Leptinotarsa* spp., *Diabrotica speciosa, Phthorimaea* spp., *Paratrioza* spp., *Agriotes* spp.

The mixtures of the invention may be used on cotton to control, for example, *Anthonomus grandis, Pectinophora* spp., *heliothis* spp., *Spodoptera* spp., *Tetranychus* spp., *Empoasca* spp., *Thrips* spp., *Bemisia tabaci, Trialeurodes* spp., Aphids, *Lygus* spp., *phyllophaga* spp., *Scaptocoris* spp., *Austroasca viridigrisea, Creontiades* spp., *Nezara* spp., *Piezodorus* spp., *Halotydeus destructor, Oxycaraenus hyalinipennis, Dysdercus cingulatus*. The mixtures of the invention are preferably used on cotton to control *Anthonomus grandis, Tetranychus* spp., *Empoasca* spp., *thrips* spp., *Lygus* spp., *phyllophaga* spp., *Scaptocoris* spp.

The mixtures of the invention may be used on rice to control, for example, *Leptocorisa* spp., *Cnaphalocrosis* spp., *Chilo* spp., *Scirpophaga* spp., *Lissorhoptrus* spp., *Oebalus pugnax, Scotinophara* spp., *Nephotettix malayanus, Nephotettix nigropictus, Nephottetix parvus, Nephotettix virescens, Nephotettix* spp., Mealybugs, *Sogatella furcifera, Nilaparvata lugens, Orseolia* spp., *Cnaphalocrocis medinalis, Marasmia* spp., *Stenchaetothrips biformis, Thrips* spp., *Hydrellia philippina*, Grasshoppers, *Pomacea canaliculata, Scirpophaga innotata, Chilo suppressalis, Chilo auricilius, Chilo polychrysus, Sesamia inferens, Laodelphax striatellus, Nymphula depunctalis, Oulema oryzae*, Stinkbugs. The mixtures of the invention are preferably used on rice to control *Leptocorisa* spp., *Lissorhoptrus* spp., *Oebalus pugnax, Nephotettix malayanus, Nephotettix nigropictus, Nephotettix parvus, Nephottetix virescens, Nephotettix* spp., *Sogatella furcifera, Stenchaetothrips biformis, Thrips* spp., *Hydrellia philippina*, Grasshoppers, *Pomacea canaliculata, Scirpophaga innotata, Chilo suppressalis, Chilo polychrysus, Oulema oryzae*.

The mixtures of the invention may be used on coffee to control, for example, *Hypothenemus Hampei, Perileucoptera Coffeella, Tetranychus* spp., *Brevipalpus* spp., Mealybugs. The mixtures of the invention are preferably used on coffee to control *Hypothenemus Hampei, Perileucoptera Coffeella*.

The mixtures of the invention may be used on citrus to control, for example, *Panonychus citri, Phyllocoptruta oleivora, Brevipalpus* spp., *Diaphorina citri, Scirtothrips* spp., *Thrips* spp., *Unaspis* spp., *Ceratitis capitata, Phyllocnistis* spp., Aphids, Hardscales, Softscales, Mealybugs. The mixtures of the invention are preferably used on citrus to control *Panonychus citri, Phyllocoptruta oleivora, Brevipalpus* spp., *Diaphorina citri, Scirtothrips* spp., *thrips* spp., *Phyllocnistis* spp.

The mixtures of the invention may be used on almonds to control, for example, *Amyelois transitella, Tetranychus* spp.

The mixtures of the invention may be used on fruiting vegetables, cucurbits and pulses, including tomatoes, pepper, chili, eggplant, cucumber, squash etc., to control, for example, *Thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Bemisia tabaci, Trialeurodes* spp., Aphids, *Paratrioza* spp., *Frankliniella occidentalis, Frankliniella* spp., *Phyllotreta* spp., *Amrasca* spp., *Epilachna* spp., *Halyomorpha* spp., *Scirtothrips* spp., *Leucinodes* spp., *Neoleucinodes* spp. *Maruca* spp., Fruit flies, Stinkbugs, Lepidopteras, Coleopteras. The mixtures of the invention are preferably used on fruiting vegetables, cucurbits and pulses, including tomatoes, pepper, chili, eggplant, cucumber, squash etc., to control *Thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Paratrioza* spp., *Frankliniella occidentalis, Frankliniella* spp., *Amrasca* spp., *Scirtothrips* spp., *Leucinodes* spp., *Neoleucinodes* spp.

The mixtures of the invention may be used on tea to control, for example, *Pseudaulacaspis* spp., *Empoasca* spp., *Scirtothrips* spp., *Caloptilia theivora, Tetranychus* spp. The mixtures of the invention are preferably used on tea to control *Empoasca* spp., *Scirtothrips* spp.

The mixtures of the invention may be used on bulb vegetables, including onion, leek etc. to control, for example, *Thrips* spp., *Spodoptera* spp., *heliothis* spp. The mixtures of the invention are preferably used on bulb vegetables, including onion, leek etc. to control *Thrips* spp.

The mixtures of the invention may be used on grapes to control, for example, *Empoasca* spp., *Lobesia* spp., *Eupoecilia ambiguella, Frankliniella* spp., *Thrips* spp., *Tetranychus* spp., *Rhipiphorothrips Cruentatus, Eotetranychus Willamettei, Erythroneura Elegantula, Scaphoides* spp., *Scelodonta strigicollis*, Mealybugs. The mixtures of the invention are preferably used on grapes to control *Frankliniella* spp., *Thrips* spp., *Tetranychus* spp., *Rhipiphorothrips Cruentatus, Scaphoides* spp.

The mixtures of the invention may be used on pome fruit, including apples, pears etc., to control, for example, *Cacopsylla* spp., *Psylla* spp., *Panonychus ulmi, Cydia pomonella*, Lepidopteras, Aphids, Hardscales, Softscales. The mixtures of the invention are preferably used on pome fruit, including apples, pears etc., to control *Cacopsylla* spp., *Psylla* spp., *Panonychus ulmi*.

The mixtures of the invention may be used on stone fruit to control, for example, *Grapholita molesta, Scirtothrips* spp., *Thrips* spp., *Frankliniella* spp., *Tetranychus* spp., Aphids, Hardscales, Softscales, Mealybugs. The mixtures of the invention are preferably used on stone fruit to control *Scirtothrips* spp., *Thrips* spp., *Frankliniella* spp., *Tetranychus* spp.

The mixtures of the invention may be used on cereals to control, for example, Aphids, Stinkbugs, earthmites, *Eurygaster integriceps, Zabrus tenebrioides, Anisoplia austriaca, Chaetocnema aridula, Phyllotreta* spp., *Oulema melanopus, Oscinella* spp., *Delia* spp., *Mayetiola* spp., *Contarinia* spp., *Cephus* spp., *Steneotarsonemus* spp., *Apamea* spp.

In another embodiment compounds of formula I and mixtures of the invention may be used on rice to control *Baliothrips biformis (Thrips), Chilo* spp. (e.g. *Chilo polychrysus* (Dark headed striped borer), *Chilo suppressalis* (Rice stemborer), *Chilo indicus* (Paddy stem borer), *Chilo polychrysus* (Dark-headed rice borer), *Chilo suppressalis* (Stripe stem borer)), *Cnaphalocrocis medinalis* (Rice leaf folder), *Dicladispa armigera* (Hispa), *Hydrellia philipina* (Rice whorl-maggot), *Laodelphax* spp. (Smaller brown planthopper) (e.g. *Laodelphax striatellus*), *Lema oryzae* (Rice leafbeetle), *Leptocorsia acuta* (Rice bug), *Leptocorsia oratorius* (rice bug), *Lissorhoptrus oryzophilus* (rice water weevil), *Mythemina separata* (armyworm), *Nephotettix* spp. (Green leafhopper) (e.g. *Nephotettix cincticeps, Nephotettix malayanus, Nephotettix nigropictus, Nephotettix parvus,*

*Nephottetix virescens*), *Nilaparvata lugens* (Brown Planthopper), *Nymphula depunctalis* (Rice caseworm), *Orseolia oryzae* (Rice Gall midge), *Oulema oryzae* (Rice leafbeetle), *Scirpophaga incertulas* (Yellow Stemborer), *Scirpophaga innotata* (White Stemborer), *Scotinophara coarctata* (Rice black bug), *Sogaella frucifera* (White-backed planthopper), *Steneotarsonemus spinki*.

The compounds of formula I and mixtures of the invention may be used to control animal housing pests including: Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Saw-toothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of formula I and mixtures of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leafminers (adults), Leaf rollers, Leaf skeletonizers, Midges, Mosquitoes, Oleander moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, *Thrips*, Tip moths, Tussock moth larvae, Wasps, Broadmites, Brown softscales, California redscales (crawlers), Clover mites, Mealybugs, Pineneedlescales (crawlers), Spider mites, Whiteflies.

The compounds of formula I and mixtures of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs.

The compounds of formula (I) and mixture of the invention, in particular those in the tables above, may be used for soil applications, including as a seed application, to target at least the following: sucking pests such as aphids, *thrips*, brown plant hopper (e.g. on rice), sting bugs, white flies (e.g. on cotton and vegetables), mites; on soil pests such as corn root worm, wireworms, white grubs, *zabrus*, termites (e.g. on sugar cane, soy, pasture), maggots, cabbage root fly, red legged earth mite; on lepidoptera, such as *spodoptera*, cutworms, *elasmoplpus, plutella* (e.g. *brassica*), stem borers, leaf miners, flea beetle, *Sternechus*; on nematicides, such as *Heterodera glycines* (e.g. on soybean), *Pratylenchus brachyurus* (e.g. on corn), *P. zeae* (e.g. on corn), *P. penetrans* (e.g. on corn), *Meloidogyne incognita* (e.g. on vegetables), *Heterodera schachtii* (e.g. on sugar beet), *Rotylenchus reniformis* (e.g. on cotton), *Heterodera avenae* (e.g. on cereals), *Pratylenchus neglectus* (e.g. on cereals), *thornei* (e.g. on cereals).

The compounds of formula (I) and mixture of the invention, in particular those in the tables above may be used for seed applications at least on the following: soil grubs for corn, soybeans, sugarcane: *Migdolus* spp; *Phyllophaga* spp.; *Diloboderus* spp; *Cyclocephala* spp; *Lyogenys fuscus*; sugarcane weevils: *Sphenophorus levis* & *Metamasius hemipterus*; termites for soybeans, sugarcane, pasture, others: *Heterotermes tenuis; Heterotermes longiceps; Cornitermes cumulans; Procornitermes triacifer; Neocapritermes opacus; Neocapritermes parvus*; corn root worms for corn and potatoes: *Diabrotica* spp., seed Maggot: *Delia platura*; soil stinkbugs: *Scaptocoris castanea*; wireworms: *Agriotes* spp; *Athous* spp *Hipnodes bicolor; Ctenicera destructor; Limonius canu; Limonius californicus*; rice water weevil: *Lissorhoptrus oryzophilus*; Red Legged earth mites: *Halotydeus destructor*.

For soil applications using compounds of formula I on sugar cane, including application on sugar cane propogation material such as buds, the following mixing partners are of particular interest: fungicides selected from N-[9-(dichloromethylene)-1,2,3,4-tetrahydro-1,4-methanonaphthalen-5-yl]-3-(difluoromethyl)-1-methyl-1H-pyrazole-4-carboxamide [CAS 1072957-71-1], azoxystrobin, cyproconazole, protioconazole, optionally in combination with insecticides selected from neonicotinoids, in particular thiamethoxam, imidacloprid and clothianidin, sulfoxaflor, abamectin, carbofuran, tefluthrin, fipronil, ethiprole, spinosad, lamda-cyhalothrin, bisamides, in particular chlorantraniliprole, cyantraniliprole, flubendiamide; optionally with fungicides selected from azoxystrobin, cyproconazole, thiabendazole, fluazinam, fludioxonil, mefenoxam, Sedaxane. For foliar applications using compounds of formula I on sugar cane, the following mixing partners are of particular interest: insecticides selected from thiamethoxam, Lambda cyhalothrin, spirotetramat, spinetoran, chlorantraniliprole, lufenuron. Combinations with glyphosate are also of interest.

The amount of a combination of the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of fungi and/or animal pest to be controlled or the application time.

The mixtures comprising a compound of formula I, e.g. those selected from table A, and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Table A and the active ingredients as described above is not essential for working the present invention.

Synergistic activity is present when the fungicidal and/or animal pesticidal activity of the composition of A+B is greater than the sum of the fungicidal and/or pesticidal activities of A and B.

The method of the invention comprises applying to the useful plants, the locus thereof or propagation material thereof in admixture or separately, a synergistically effective aggregate amount of a component A and a component B.

Some of said combinations according to the invention have a systemic action and can be used as foliar, soil and seed treatment pesticides.

With the combinations according to the invention it is possible to inhibit or destroy the phytopathogenic microorganisms and/or animal pests which occur in plants or in parts of plants (fruit, blossoms, leaves, stems, tubers, roots) in different useful plants, while at the same time the parts of plants which grow later are also protected from attack by phytopathogenic microorganisms and/or animal pests.

The combinations of the present invention are of particular interest for controlling a large number of fungi and/or animal pests in various useful plants or their seeds, especially in field crops such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and cucurbits.

The combinations according to the invention are applied by treating the fungi and/or animal pests, the useful plants, the locus thereof, the propagation material thereof, the natural substances of plant and/or animal origin, which have been taken from the natural life cycle, and/or their processed forms, or the industrial materials threatened by fungus and/or animal pests, attack with a combination of components A and B in a synergistically effective amount.

The combinations according to the invention may be applied before or after infection or contamination of the useful plants, the propagation material thereof, the natural substances of plant and/or animal origin, which have been taken from the natural life cycle, and/or their processed forms, or the industrial materials by the fungi and/or animal pests.

When applied to the useful plants the compound of formula I is applied at a rate of 1 to 500 g a.i./ha in association with 1 to 5000 g a.i./ha, particularly 1 to 2000 g a.i./ha, of a compound of component B, depending on the class of chemical employed as component B.

Generally for plant propagation material, such as seed treatment, application rates can vary from 0.001 to 10 g/kg of seeds of active ingredients for compounds of formula I. When the combinations of the present invention are used for treating seed, rates of 0.001 to 5 g of a compound of formula I per kg of seed, preferably from 0.01 to 1 g per kg of seed, and 0.001 to 50 g of a compound of component B, per kg of seed, preferably from 0.01 to 10 g per kg of seed, are generally sufficient.

The weight ratio of A to B may generally be between 1000:1 and 1:1000. In other embodiments that weight ratio of A to B may be between 500:1 to 1:500, for example between 100:1 to 1:100, for example between 1:50 to 50:1, for example 1:20 to 20:1. Other examples of weight ratios of A to B include 4000:1 or less, e.g. 1000:1 or less, e.g. 100:1 or less. For example 1:250 to 250:1, e.g. 1:100 to 100:1, e.g. 100:1 to 1:10, e.g. 100:1 to 1:1, e.g. 50:1 to 1:1. Other embodiments include 1:5 to 5:1, for example 4:1, 3:1, 2:1, 1:1, 1:2, 1:3, 1:4, 1:5

The invention also provides pesticidal mixtures comprising a combination of components A and B as mentioned above in a synergistically effective amount, together with an agriculturally acceptable carrier, and optionally a surfactant.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules. A typical a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation. A typical pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

The rates of application of a plant propagation material treatment varies, for example, according to type of use, type of crop, the specific compound(s) and/or agent(s) used, and type of plant propagation material. The suitable rate is an effective amount to provide the desired action (such as disease or pest control) and can be determined by trials and routine experimentation known to one of ordinary skill in the art.

Generally for soil treatments, application rates can vary from 0.05 to 3 kg per hectare (g/ha) of ingredients. Generally for seed treatments, application rates can vary from 0.5 to 1000 g/100 kg of seeds of ingredients.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula I together with a compound of component B, and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

FORMULATION EXAMPLES

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, seeds can be treated and protected against infestation by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, seeds can be treated and protected against infestation by spraying, pouring or immersion.

The invention further pertains to a product for use in agriculture or horticulture comprising a capsule wherein at least a seed treated with the inventive compound is located. In another embodiment, the product comprises a capsule wherein at least a treated or untreated seed and the inventive compound are located.

Slow Release Capsule Suspension 28 parts of the inventive compound are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredient. The medium capsule diameter is 8-15 microns. The resulting formulation is applied to seeds as an aqueous suspension in a suitable apparatus.

EXAMPLES

The Examples in PCT/EP2010/068605, incorporated herein by reference, demonstrates that compounds of formula I have inseciticidal activity.

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms the synergism factor SF corresponds to O/E. In the agricultural practice an SF of $\geq 1.2$ indicates significant improvement over the purely complementary addition of activities (expected activity), while an SF of $\leq 0.9$ in the practical application routine signals a loss of activity compared to the expected activity.

Tables 1 to 3 show mixtures of the present invention demonstrating notable synergistic effects. As insecticides do not normally have fungicidal activity, the unexpected increase in fungicidal efficacy due to the presence of the compound of formula I is truly remarkable.

*Gaeumannomyces graminis:*

Mycelial fragments of the fungus from cryogenic storage were directly mixed into nutrient broth (potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hours at 620 nm. Application rates are shown in Table 1. Two replicates per treatment were evaluated.

TABLE 1

| A58 application rate ppm | azoxystrobin application rate ppm | Observed control % | Expected control % |
|---|---|---|---|
| 20 | — | 0.0 | — |
| 10 | — | 0.0 | — |
| 5 | — | 0.0 | — |
| 2.5 | — | 0.0 | — |
| 1.2500 | — | 0.0 | — |
| 0.6250 | — | 0.0 | — |
| — | 2.0000 | 50.0 | — |
| — | 1.0000 | 50.0 | — |
| — | 0.5000 | 50.0 | — |
| — | 0.2500 | 20.0 | — |
| — | 0.1250 | 20.0 | — |
| — | 0.0625 | 0.0 | — |
| 20 | 2.0000 | 100.0 | 50.0 |
| 20 | 1.0000 | 100.0 | 50.0 |
| 20 | 0.5000 | 100.0 | 50.0 |
| 10 | 2.0000 | 100.0 | 50.0 |
| 10 | 1.0000 | 100.0 | 50.0 |
| 10 | 0.5000 | 100.0 | 50.0 |
| 10 | 0.2500 | 100.0 | 20.0 |
| 5 | 2.0000 | 100.0 | 50.0 |
| 5 | 1.0000 | 100.0 | 50.0 |
| 5 | 0.5000 | 100.0 | 50.0 |
| 5 | 0.2500 | 100.0 | 20.0 |
| 5 | 0.1250 | 90.0 | 20.0 |
| 2.5 | 1.0000 | 100.0 | 50.0 |
| 2.5 | 0.5000 | 90.0 | 50.0 |
| 2.5 | 0.2500 | 90.0 | 20.0 |
| 2.5 | 0.1250 | 70.0 | 20.0 |
| 2.5 | 0.0625 | 70.0 | 0.0 |
| 1.25 | 0.5000 | 90.0 | 50.0 |
| 1.25 | 0.2500 | 70.0 | 20.0 |
| 1.25 | 0.1250 | 70.0 | 20.0 |
| 1.25 | 0.0625 | 50.0 | 0.0 |
| 0.6250 | 0.2500 | 70.0 | 20.0 |
| 0.6250 | 0.1250 | 50.0 | 20.0 |

*Septoria tritici* (Leaf Blotch):

Conidia of the fungus from cryogenic storage were directly mixed into nutrient broth (potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hours. Application rates are shown in Table 2. Two replicates per treatment were evaluated.

TABLE 2

| A58 application rate ppm | cypropconazole application rate ppm | Observed control % | Expected control % |
|---|---|---|---|
| 20 | — | 0.0 | — |
| 10 | — | 0.0 | — |
| 5 | — | 0.0 | — |
| 2.5 | — | 0.0 | — |
| 1.2500 | — | 0.0 | — |
| — | 2.0000 | 90.0 | — |
| — | 1.0000 | 90.0 | — |
| — | 0.5000 | 70.0 | — |
| — | 0.2500 | 0.0 | — |
| — | 0.1250 | 0.0 | — |
| — | 0.0625 | 0.0 | — |
| 20 | 2.0000 | 100.0 | 90.0 |
| 20 | 1.0000 | 100.0 | 90.0 |
| 20 | 0.5000 | 100.0 | 70.0 |
| 10 | 2.0000 | 100.0 | 90.0 |
| 10 | 1.0000 | 100.0 | 90.0 |
| 10 | 0.5000 | 100.0 | 70.0 |
| 10 | 0.2500 | 100.0 | 0.0 |
| 5 | 2.0000 | 100.0 | 90.0 |
| 5 | 1.0000 | 100.0 | 90.0 |
| 5 | 0.5000 | 100.0 | 70.0 |
| 5 | 0.2500 | 90.0 | 0.0 |
| 5 | 0.1250 | 20.0 | 0.0 |
| 2.5 | 1.0000 | 100.0 | 90.0 |
| 2.5 | 0.5000 | 100.0 | 70.0 |
| 2.5 | 0.2500 | 90.0 | 0.0 |
| 1.25 | 0.5000 | 100.0 | 70.0 |
| 1.25 | 0.2500 | 90.0 | 0.0 |

*Mycosphaerella arachidis* (syn. *Cercospora arachidicola*),

Brown leaf spot of groundnut (peanut): Conidia of the fungus from cryogenic storage were directly mixed into nutrient broth (potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after approximately 5-6 days at 620 nm. Application rates are shown in Table 3. Two replicates per treatment were evaluated

TABLE 3

| A58 application rate ppm | C-IIIA application rate ppm | Observed control % | Expected control % |
|---|---|---|---|
| 1.2500 | — | 0.0 | — |
| 0.6250 | — | 0.0 | — |
| 0.3125 | — | 0.0 | — |
| 0.1563 | — | 0.0 | — |
| 0.078125 | — | 0.0 | — |
| 0.0390625 | — | 0.0 | — |
| — | 0.0313 | 90.0 | — |
| — | 0.0156 | 20.0 | — |
| 1.25 | 0.0313 | 100.0 | 90.0 |
| 0.6250 | 0.0156 | 50.0 | 20.0 |
| 0.3125 | 0.0156 | 50.0 | 20.0 |
| 0.1563 | 0.0156 | 50.0 | 20.0 |
| 0.078125 | 0.0156 | 70.0 | 20.0 |
| 0.0390625 | 0.0156 | 70.0 | 20.0 |

C-IIIA refers to the compound of formula IIIA.

*Pythium ultimum* (Damping Off):

Mycelial fragments of the fungus, prepared from a fresh liquid culture, were directly mixed into nutrient broth (potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hours.

*Rhizoctonia solani* (Foot Rot, Damping-Off):

Mycelial fragments of the fungus from cryogenic storage were directly mixed into nutrient broth (potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hours.

*Gaeumannomyces graminis:*

Mycelial fragments of the fungus from cryogenic storage were directly mixed into nutrient broth (potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hours at 620 nm.

*Monographella nivalis* (syn. *Microdochium nivale, Fusarium nivale*), snow mould, foot rot: Conidia of the fungus from cryogenic storage were directly mixed into nutrient broth (potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hours at 620 nm.

*Botrytis cinerea* (Gray Mould):

Conidia of the fungus from cryogenic storage were directly mixed into nutrient broth (potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hours.

*Glomerella lagenarium* (syn. *Colletotrichum lagenarium*),

Anthracnose of cucurbits: Conidia of the fungus from cryogenic storage were directly mixed into nutrient broth (potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hours at 620 nm.

*Fusarium culmorum* (Root Rot):

Conidia of the fungus from cryogenic storage were directly mixed into nutrient broth (potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hrs.

The invention claimed is:

1. A pesticidal mixture comprising a component A and a component B, wherein component A is a compound of formula I

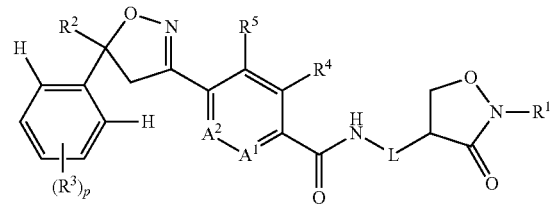

wherein

L is a direct bond or methylene;

$A^1$ and $A^2$ are C-H;

$R^1$ is hydrogen $C_1$-$C_8$alkyl, or $C_1$-$C_8$haloalkyl;

$R^2$ is chlorodifluoromethyl or trifluoromethyl;

each $R^3$ is independently bromo, chloro, fluoro or trifluoromethyl;

$R^4$ is hydrogen, halogen, methyl, halomethyl or cyano;

$R^5$ is hydrogen;

p is 2 or 3;

and component B is a fungicide selected from azoxystrobin, cyproconazole, and a compound of formula IIIA

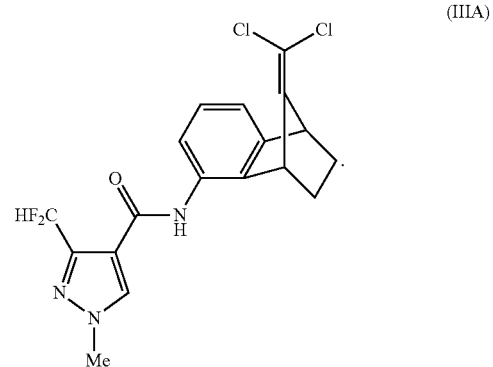

2. A pesticidal mixture according to claim 1, wherein component A is a mixture of compounds I* and I**

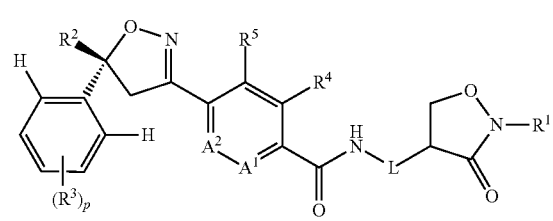

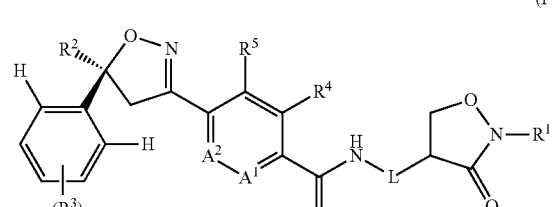

wherein the molar proportion of compound I** compared to the total amount of both enantiomers is greater than 50%.

3. A pesticidal mixture according to claim 1, wherein the mixture further comprises an agricultural acceptable carrier and optionally a surfactant.

4. A pesticidal mixture according to claim 1, wherein the weight ratio of A to B is 1000:1 to 1:1000.

5. A pesticidal mixture according to claim 1, wherein the weight ratio of A to B is 100:1 to 1:10.

6. A method of controlling phytopathogenic diseases on useful plants or on propagation material thereof, which comprises applying to the useful plants, the locus thereof or propagation material thereof the mixture of claim 1.

7. A method of controlling insects, acarines, nematodes or molluscs which comprises applying to a pest, to a locus of a pest, or to a plant susceptible to attack by a pest the mixture of claim 1.

8. A seed comprising a pesticidal mixture as defined in claim 1.

9. A method comprising coating a seed with a mixture as defined in claim 1.

* * * * *